(12) United States Patent
Bryan

(10) Patent No.: US 6,541,235 B1
(45) Date of Patent: Apr. 1, 2003

(54) CALCIUM FREE SUBTILISIN MUTANTS

(75) Inventor: Philip N. Bryan, North Potomac, MD (US)

(73) Assignee: University of Maryland Biotechnology Institute, Baltimore, MD (US)

(*) Notice: Subject to any disclaimer, the term of this patent is extended or adjusted under 35 U.S.C. 154(b) by 117 days.

(21) Appl. No.: 09/672,105

(22) Filed: Sep. 29, 2000

(51) Int. Cl.⁷ .............................. C12N 9/54; C12N 9/56; C12N 15/57; C12N 15/74; C12N 15/75

(52) U.S. Cl. ...................... 435/221; 435/69.1; 435/222; 435/252.3; 435/320.1; 435/471; 536/23.2

(58) Field of Search .................. 435/69.1, 222, 435/471, 252.3, 320.1; 536/23.2

(56) References Cited

U.S. PATENT DOCUMENTS

| | | | |
|---|---|---|---|
| 4,908,773 A | * 3/1990 | Pantoliano et al. | 702/138 |
| 4,914,031 A | * 4/1990 | Zukowski et al. | 435/222 |
| 4,980,288 A | * 12/1990 | Bryan et al. | 435/222 |
| 4,990,425 A | * 2/1991 | Bryan et al. | 435/222 |
| 5,013,657 A | * 5/1991 | Bryan et al. | 435/222 |
| 5,116,741 A | * 5/1992 | Bryan et al. | 435/222 |
| 5,246,849 A | * 9/1993 | Bryan et al. | 435/220 |
| 5,260,207 A | * 11/1993 | Pantoliano et al. | 435/220 |
| 5,275,945 A | * 1/1994 | Hsiao et al. | 435/221 |
| 5,310,675 A | * 5/1994 | Estell et al. | 435/320.1 |
| 5,316,941 A | * 5/1994 | Estell et al. | 435/252.3 |
| 5,324,653 A | * 6/1994 | van Eekelen et al. | 435/221 |
| 5,336,611 A | * 8/1994 | van Eekelen et al. | 435/221 |
| 5,340,735 A | * 8/1994 | Christianson et al. | 435/221 |
| 5,346,823 A | * 9/1994 | Estell et al. | 435/221 |
| 5,352,603 A | * 10/1994 | Vetter et al. | 435/221 |
| 5,371,008 A | * 12/1994 | Carter et al. | 435/220 |
| 5,371,190 A | * 12/1994 | Carter et al. | 530/350 |
| 5,389,307 A | * 2/1995 | Lindegaard et al. | 510/320 |
| 5,403,737 A | * 4/1995 | Abrahmsen et al. | 435/252.3 |
| 5,441,882 A | * 8/1995 | Estell et al. | 435/222 |

(List continued on next page.)

OTHER PUBLICATIONS

Svendsen et al., *FEBS Letters*, 196(2):228–232 (1986).

Jany et al., *FEBS Letters*, 199(2):139–144 (1986).

Vasantha et al., *Journal of Bacteriology*, 159(3):811–819 (1984).

Kurihara et al., *The Journal of Biological Chemistry*, 247(17):5619–5631 (1972).

Gros et al., *The Journal of Biological Chemistry*, 266(5):2953–2961 (1991).

*Journal of Cellular Biochemistry*, UCLA Symposia on Molecular & Cellular Biology, Supplement 10A, p. 272, Abstract E105 (1986).

Holmes et al., *J. Mol. Biol.*, 160:623–639 (1982).

Betzel et al., *J. Mol. Biol.*, 223:427–445 (1992).

Zoller et al., *Methods in Enzymology*, 100:468–500 (1983).

Privalov et al., *Methods in Enzymology*, 131:4–51 (1986).

Wells et al., *Nucleic Acids Research*, 11(22):7911–7925 (1983).

Jacobs et al., *Nucleic Acids Research*, 13(24):8913–8926 (1985).

(List continued on next page.)

*Primary Examiner*—Ponnathapu Achutamurthy
*Assistant Examiner*—William W. Moore
(74) *Attorney, Agent, or Firm*—Marianne Fuierer; Steven J. Hultquist; Yongzhi Yang

(57) ABSTRACT

Novel calcium free subtilisin mutants are taught, in particular subtilisins which have been mutated to eliminate amino acids 75–83 and part or all of amino acids 1–22 (the N-terminal region) and which retain enzymatic activity and stability. Recombinant methods for producing the same and recombinant DNA encoding for such subtilisin mutants are also provided.

14 Claims, 13 Drawing Sheets

U.S. PATENT DOCUMENTS

| | | | | |
|---|---|---|---|---|
| 5,453,372 A | * | 9/1995 | Vetter et al. | 435/222 |
| 5,470,733 A | * | 11/1995 | Bryan et al. | 435/222 |
| 5,472,855 A | * | 12/1995 | Carter et al. | 435/68.1 |
| 5,482,849 A | * | 1/1996 | Branner et al. | 435/222 |
| 5,500,364 A | * | 3/1996 | Christianson et al. | 435/221 |
| 5,567,601 A | * | 10/1996 | Bryan et al. | 435/222 |
| 5,629,173 A | * | 5/1997 | Abrahmsen et al. | 435/69.1 |
| 5,631,217 A | * | 5/1997 | Branner et al. | 510/320 |
| 5,652,136 A | * | 7/1997 | Carter et al. | 435/252.3 |
| 5,677,272 A | * | 10/1997 | Ghosh et al. | 510/306 |
| 5,679,630 A | * | 10/1997 | Baeck et al. | 510/305 |
| 5,707,848 A | * | 1/1998 | Bryan et al. | 435/8 |
| 5,736,512 A | * | 4/1998 | Abrahmsen et al. | 514/12 |
| 5,741,664 A | * | 4/1998 | Ballinger et al. | 435/68.1 |
| 5,741,694 A | * | 4/1998 | Hastrup et al. | 435/222 |
| 5,763,257 A | * | 6/1998 | Bott et al. | 435/221 |
| 5,801,038 A | * | 9/1998 | Bott et al. | 435/221 |
| 5,801,039 A | * | 9/1998 | Maurer et al. | 435/221 |
| 5,955,340 A | * | 9/1999 | Bott et al. | 435/221 |
| 5,972,682 A | * | 10/1999 | Bott et al. | 435/221 |
| 5,985,639 A | * | 11/1999 | Christianson et al. | 435/221 |
| 6,197,567 B1 | * | 3/2001 | Aaslyng et al. | 435/221 |
| 6,197,589 B1 | * | 3/2001 | Maurer et al. | 435/221 |
| 6,271,012 B1 | * | 8/2001 | van Eekelen et al. | 435/221 |
| 6,287,841 B1 | * | 9/2001 | Mulleners et al. | 435/221 |

OTHER PUBLICATIONS

Bryan et al., *Proc. Natl. Acad. Sci.*, 83:3743–3745 (1986).
Vita et al., *Protein Engineering*, 1(3):265 (1987).
Cunningham et al., *Protein Engineering*, 1(4):319–325 (1987).
Betzel et al., *Protein Engineering*, 3(3):161–172 (1990).
Siezen et al., *Protein Engineering*, 4(7):719–737 (1991).
Bryan et al., *Proteins: Structure, Function, and Genetics*, 1:326–334 (1986).
Frommel et al., *Proteins: Structure, Function and Genetics*, 5:22–37 (1989).
Heiner et al., *Proteins: Structure, Function and Genetics*, 14:451–464 (1992).
Gallagher et al., *Proteins: Structure, Function and Genetics*, 16:205–213 (1993).
Wells et al., *Trends in Biochemical Sciences*, 13:291–297 (1988).
Bryan et al., *Biotechnology Research and Applications*, Gavora, J., et al., Eds. Elsevier Publishing Co., 57–67 (1988).
Bryan, "Engineering Dramatic Increases in the Stability of Subtilisin", *Stability of Protein Pharmaceuticals, Part B: In Vivo Pathways of Degradation and Strategies for Protein Stabilization*, eds. Tim J. Ahern and Mark C. Manning, Chapter 5, pp. 147–181 (1992).
Privalov et al., *Advances in Protein Chemistry*, 39:191–233 (1988).
Wiseman et al., *Analytical Biochemistry*, 179:131–137 (1989).
Deleage et al., *Analytical Biochemistry*, 163:292–297 (1987).
Fahnestock et al., *Applied and Environmental Microbiology*, 53(2):379–384 (1987).
Carrara et al., *Archives of Biochemistry and Biophysics*, 294(1):107–114 (1992).
Voordouw et al., *Biochemistry*, 15(17):3716–3724 (1976).
McPhalen et al., *Biochemistry*, 26:261–269 (1987).
Pantoliano et al., *Biochemistry*, 26:2077–2082 (1987).
McPhalen et al., *Biochemistry*, 27:6582–6598 (1988).
Pantoliano et al., *Biochemistry*, 27:8311–8317 (1988).
Chen et al., *Biochemistry*, 28:691–699 (1989).
Pantoliano et al., *Biochemistry*, 28:7205–7213 (1989).
Abrahmsen et al., *Biochemistry*, 30:4151–4159 (1991).
Livingstone et al., *Biochemistry*, 30:4237–4244 (1991).
Bryan et al, *Biochemistry*, 31:4937–4945 (1992).
Braxton et al., *Biochemistry*, 31:7796–7801 (1992).
Eder et al., *Biochemistry*, 32:18–26 (1993).
Strausberg et al., *Biochemistry*, 32:8112–8119 (1993).
Bryant, *Biochem J.*, 226:613–616 (1985).
Nedkov et al., *Biol. Chem. Hoppe–Seyler*, 366:421–430 (1985).
Narhi et al., *Biotechnology and Applied Biochemistry*, 13:12–24 (1991).
Rollence et al., *CRC Critical Reviews in Biotechnology*, 8(3):217–224 (1988).
Meloun et al., *FEBS Letters*, 183(2):195–200 (1985).

* cited by examiner

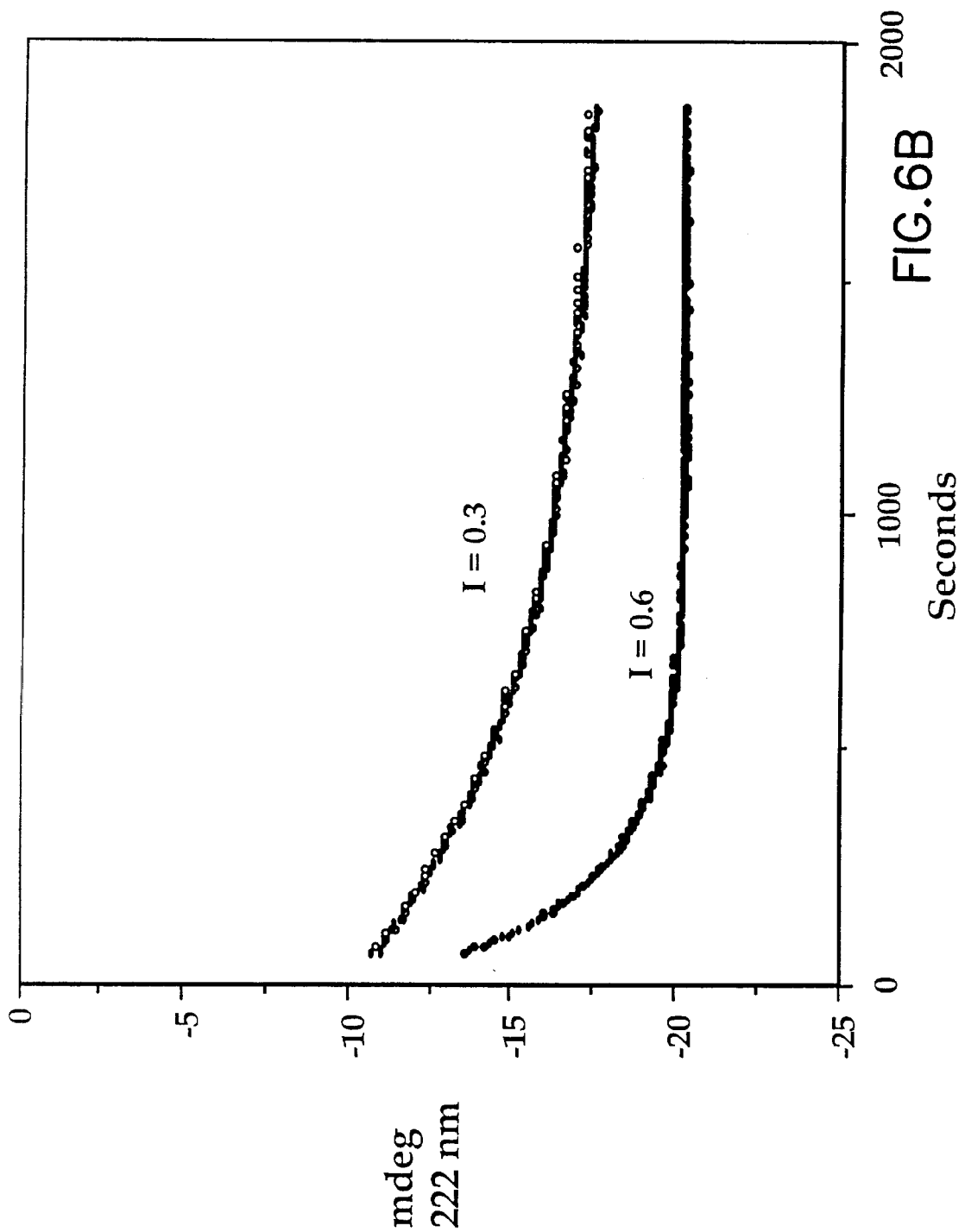

CALCIUM FREE SUBTILISIN MUTANTS

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. GM42560 awarded by National Institute of Health.

GENERAL OBJECTS OF THE INVENTION

A general object of the invention is to provide subtilisin mutants which have been mutated such that they do not bind calcium.

Another object of the invention is to provide DNA sequences which upon expression provide for subtilisin mutants which do not bind calcium.

Another object of the invention is to provide subtilisin mutants which comprise specific combinations of mutations which provide for enhanced thermal stability.

Another object of the invention is to provide a method for the synthesis of a subtilisin mutant which does not bind calcium-by the expression of a subtilisin DNA which comprises one or more substitution', deletion or addition mutations in a suitable recombinant host cell.

A more specific object of the invention is to provide class I subtilase mutants, in particular BPN', mutants which have been mutated such that they do not bind calcium.

Another specific object of the invention is to provide DNA sequences which upon expression result in class I subtilase mutants, and in particular BPN' mutants which do not bind calcium.

Another specific object of the invention is to provide a method for making subtilisin I-S1 or I-S2 mutants, and in particular BPN' mutants which do not bind calcium by expression of a class I subtilase mutant DNA sequence, and more specifically a BPN' DNA coding sequence which comprises one or more substitution, addition or deletion mutations in a suitable recombinant host cell.

Yet another specific object of the invention is to provide mutant subtilisin I-S1 or I-S2, and more specifically BPN' mutants which do not bind calcium and which further comprise particular combinations of mutations which provide for enhanced thermal stability, or which restore cooperativity to the folding reaction.

Yet a further object of the invention is to provide a mutant subtilisin protein which has the calcium binding loop deleted (i.e. amino acids 75–83) and deletion of amino acids in the N-terminal region (amino acids 1–22). It was discovered that when the calcium binding loop was deleted, the N-terminal part of the molecule is no longer absolutely required for proper folding.

The subtilisin mutants of the present invention are to be utilized in applications where subtilisins find current usage. Given that these mutants do not bind calcium they should be particularly well suited for use in industrial environments which comprise chelating agents, e.g. detergent compositions, which substantially reduces the activity of wild-type calcium binding subtilisins.

BACKGROUND OF THE INVENTION (1) Field of the Invention

The present invention relates to subtilisin proteins which have been modified to eliminate calcium binding. More particularly, the present invention relates to novel subtilisin I-S1 and I-S2 subtilisin mutants, specifically BPN' mutants wherein the calcium A-binding loop has been deleted, specifically wherein amino acids 75–83 have been deleted, and which may additionally comprise one or more other mutations, e.g., subtilisin modifications, which provide for enhanced thermal stability and/or mutations which restore cooperativity to the folding reaction. Most particularly, the present invention relates to subtilisin proteins which have been modified to eliminate calcium binding and to delete the N-terminal region of the protein.

(2) Description of the Related Art

Subtilisin is an unusual example of a monomeric protein with a substantial kinetic barrier to folding and unfolding. A well known example thereof, subtilisin BPN' is a 275 amino acid serine protease secreted by *Bacillus amyloliquefaciens*. This enzyme is of considerable industrial importance (such as for biodegradable cleaning agents in laundry detergent) and has been the subject of numerous protein engineering studies (Siezen et al., *Protein Engineering* 4:719–737 (1991); Bryan, *Pharmaceutical Biotechnology* 3(B):147181 (1992); Wells et al., *Trends Biochem.* Sci. 13:291–297 (1988)). The amino acid sequence for subtilisin BPN' is known in the art and may be found in Vasantha et al., *J. Bacteriol.* 159:811–819 (1984). The amino acid sequence as found therein is hereby incorporated by reference [SEQUENCE ID NO:1]. Throughout the application, when Applicants refer to the amino acid sequence of subtilisin BPN' or its mutants, they are referring to the amino acid sequence as listed therein.

Subtilisin is a serine protease produced by Gram positive bacteria or by fungi. The amino acid sequences of numerous subtilisins are known. (Siezen et al., *Protein Engineering* 4:719–737 (1991)). These include five subtilisins from Bacillus strains, for example, subtilisin BPN', subtilisin Carlsberg, subtilisin DY, subtilisin amylosacchariticus, and mesenticopeptidase. (Vasantha et al., "Gene for alkaline protease and neutral protease from *Bacillus amyloliquefaciens* contain a large open-reading frame between the regions coding for signal sequence and mature protein," *J. Bacteriol.* 159:811–819 (1984); Jacobs et al., "Cloning sequencing and expression of subtilisin Carlsberg from Bacillus licheniformis, *Nucleic Acids Res.* 13:8913–8926 (1985); Nedkov et al.," Determination of the complete amino acid sequence of subtilisin DY and its comparison with the primary structures of the subtilisin BPN', Carlsberg and amylosacchariticus, Biol. Chem. Hoope-Seyler 366:421–430 (1985); Kurihara et al., "Subtilisin amylosacchariticus," *J. Biol. Chem.* 247:5619–5631 (1972); and Svendsen et al., "Complete amino acid sequence of alkaline mesentericopeptidase," *FEBS Lett.* 196:228–232 (1986)).

The amino acid sequences of subtilisins from two fungal proteases are known: proteinase K from *Tritirachium albam* (Jany et al., "Proteinase K from Tritirachium albam Limber," *Biol. Chem. Hoppe-Seyler* 366:485492 (1985)) and thermomycolase from the thermophilic fungus, *Malbranchea pulchella* (Gaucher et al., "Endopeptidases: Thermomycolin," *Methods Enzymol.* 45:415433 (1976)).

These enzymes have been shown to be related to subtilisin BPN', not only through their primary sequences and enzymological properties, but also by comparison of x-ray crystallographic data. (McPhalen et al., "Crystal and molecular structure of the inhibitor eglin from leeches in complex with subtilisin Carlsberg," *FEBS Lett.*, 188:55–58 (1985) and Pahler et al., "Three-dimensional structure of fungal proteinase K reveals similarity to bacterial subtilisin," *EMBO J.* 3:1311–1314 (1984)).

Subtilisin BPN' is an example of a particular subtilisin gene secreted by *Bacillus amyloliquefaciens*. This gene has been cloned, sequenced and expressed at high levels from its natural promoter sequences in *Bacillus subtilis*. The subtilisin BPN' structure has been highly refined (R=0.14) to 1.3 Å resolution and has revealed structural details for two ion binding sites (Finzel et al., *J. Cell. Biochem. Suppl.* 10A:272 (1986); Pantoliano et al., *Biochemistry* 27:8311–8317 (1988); McPhalen et al., *Biochemistry* 27: 6582–6598 (1988)). One of these (site A) binds $Ca^{2+}$ with high affinity and is located near the N-terminus, while the other (site B) binds calcium and other cations much more weakly and is located about 32 aa away (FIG. 1). In subtilisin BPN', calcium binds to site A with an affinity of $-10^7$ $M^{-1}$ (Bryan et al, *Biochemistry* 31:4937–4945 (1992)). By binding at a specific site in the tertiary structure, calcium contributes its binding energy to the stability of the native state and makes a large contribution to the overall free energy of folding (Schellman, *Biopolymers* 14:999–1018 (1975)). Structural evidence for two calcium binding sites was also reported by Bode et al., *Eur. J. Biochem.* 166:673–692 (1987) for the homologous enzyme, subtilisin Carlsberg.

Further in this regard, the primary calcium binding site in all of the subtilisins in groups I-S1 and I-S2 (Siezen et al., 1991, Table 7) are formed from almost identical nine residue loops in the identical position of helix C. X-ray structures of the I-S1 subtilisins BPN' and Carlsberg, as well as the I-S2 subtilisin Savinase, have been determined to high resolution. A comparison of these structures demonstrates that all three have almost identical calcium A-sites.

The x-ray structure of the class I subtilase, thermitase from *Thermoactinomyces vulgaris*, is also known. Though the overall homology of BPN' to thermitase is much lower than the homology of BPN' to I-S1 and I-S2 subtilisins, thermitase has been shown to have an analogous calcium A-site. In the case of thermitase, the loop is a ten residue-interruption at the identical site in helix C.

Calcium binding sites are common features of extracellular microbial proteases probably because of their large contribution to both thermodynamic and kinetic stability (Matthews et al., *J. Biol. Chem.* 249:8030–8044 (1974); Voordouw et al., *Biochemistry* 15:3716–3724 (1976); Betzel et al., Protein Engineering 3:161–172 (1990); Gros et al., *J. Biol. Chem.* 266:2953–2961 (1991)). The thermodynamic and kinetic stability of subtilisin is believed to be necessitated by the rigors of the extracellular environment into which subtilisin is secreted, which by virtue of its own presence is protease-filled. Accordingly, high activation barriers to unfolding may be essential to lock the native conformation and prevent transient unfolding and proteolysis.

Unfortunately, the major industrial uses of subtilisins are in environments containing high concentrations of metal chelators, which strip calcium from subtilisin and compromise its stability. The rate-determining step in the inactivation of subtilisin, under strongly chelating conditions, is the loss of calcium from site A (Bryan et al, *Biochemistry* 31:4937–4945 (1992); Voordouw, *Biochem.* 15:3716–3724 (1976)). Presumably, natural protein structures evolve to be stable in the native environment, therefore alternative structural solutions should be possible which are better suited to new environments. It would, therefore, be of great practical significance to create a highly stable subtilisin which is independent of calcium.

The present inventors have previously used several strategies to increase the stability of subtilisin to thermal denaturation by assuming simple thermodynamic models to approximate the unfolding transition (Pantoliano et al., *Biochemistry* 26:2077–2082 (1987); Pantoliano et al., *Biochemistry* 27:8311–8317 (1988); Pantoliano et al., *Biochemistry* 28:7205–7213 (1989); Rollence et al., *CRC Crit. Rev. Biotechnol.* 8:217–224 (1988). However, improved subtilisin mutants which are stable in industrial environments, e.g., which comprise metal chelators, and which do not bind calcium, are currently not available.

OBJECTS AND SUNIMARY OF THE INVENTION

Accordingly, it is an object of the invention to provide mutated or modified subtilisin enzymes, e.g., class I subtilases, which have been modified to eliminate calcium binding. As used in this invention, the term "mutated or modified subtilisin" is meant to include any serine protease enzyme which has been modified to eliminate calcium binding. This includes, in particular, subtilisin BPN' and serine proteases which are homologous to subtilisin BPN', in particular class I subtilases. However, as used herein, and under the definition of mutated or modified subtilisin enzyme, the mutations of this invention may be introduced into any serine protease which has at least 50%, and preferably 80% amino acid sequence identity with the sequences-referenced above for subtilisin BPN', subtilisin Carlsberg, subtilisin DY, subtilisin amylosacchariticus, mesenticopeptidase, thermitase, or Savinase and, therefore, may be considered homologous.

The mutated subtilisin enzymes of this invention are more stable in the presence of metal chelators and may also comprise enhanced thermal stability in comparison to native or wild-type subtilisin. Thermal stability is a good indicator of the overall robustness of a protein. Proteins of high thermal stability often are stable in the presence of chaotropic agents, detergents, and under other conditions, which normally tend to inactivate proteins. Thermally stable proteins are, therefore, expected to be useful for many industrial and therapeutic applications in which resistance to high temperature, harsh solvent conditions or extended shelf-life is required.

It has been further discovered that combining individual stabilizing mutations in subtilisin frequently results in approximately additive increases in the free energy of stabilization. Thermodynamic stability has also been shown to be related to resistance to irreversible inactivation at high temperature and high pH. The single-site changes of this invention individually do not exceed a 1.5 Kcal/mol contribution to the free energy of folding. However, these small incremental increases in the free energy of stabilization result in dramatic increases in overall stability when mutations are combined, since the total free energy of folding for most proteins is in the range of 5–15 Kcals/mol (Creighton, *Proteins: Structure and Molecular Properties*, W.H. Freeman and Company, New York (1984)).

X-ray crystallographic analysis of several combination mutants reveals that conformational changes associated with each mutation tend to be highly localized with minimal distortion of the backbone structure. Thus, very large increases in stability can be achieved with no radical changes in the tertiary protein structure and only minor independent alterations in the amino acid sequence. As previously suggested (Holmes et al, *J. Mol. Biol.* 160:623 (1982)), contributions to the free energy of stabilization can be gained in different ways, including improved hydrogen bonding and hydrophobic interactions in the folded form and decreased chain entropy of the unfolded enzyme. This is significant since thermostable enzymes generally have more extended half-lives at broader temperature ranaes, thereby improving bio-reactor and shelf-life performance.

As noted supra, the invention provides subtilisin mutants which comprise one or more deletion, substitution or addition mutations which provide for the elimination of calcium binding. Preferably, this will be effected by deletion, substitution or insertion of amino acids into the calcium A-site, which in the case of class I subtilases comprises 9 amino acid residues in helix C. In the case of subtilisin BPN', the subtilisin mutants will preferably comprise one or more addition, deletion or substitution mutations of the amino acids at positions 75–83, and most preferably will comprise the deletion of amino acids 75–83, of SEQUENCE ID NO: 1. The deletion of amino acids 75–83 has been discovered to effectively eliminate calcium binding to the resultant subtilisin mutant while still providing for subtilisin BPN' proteins having enzymatic activity.

Such subtilisin mutants lacking amino acids 75–83 of SEQUENCE ID NO: 1 may further include one or more additional amino acid mutations in the sequence, e.g., mutations which provide for reduced proteolysis. It is another object of the invention to produce subtilisin mutants lacking calcium binding activity which have been further mutated to restore cooperativity to the folding reaction and thereby enhance proteolytic stability. It is another object of the invention to provide thermostable subtilisin mutants which further do not bind calcium and comprise specific combinations of mutations which provide for substantially enhanced thermal stability.

In particular, the subtilisin mutants of the present invention will include subtilisins from Bacillus strains, such as subtilisin BPN', subtilisin Carlsberg, subtilisin DY, subtilisin amylosachariticus and subtilisin mesenticopeptidase, which comprise one or more deletion, substitution or addition mutations.

The present invention further provides for subtilisin mutants lacking amino acids 75–83 of SEQUENCE ID NO: 1, which have new protein-protein interactions engineered in the regions around the deletion leading to large improvements in stability. More specifically, mutations at ten specific sites in subtilisin BPN' and its homologues are provided, seven of which individually, and in combination, have been found to increase the stability of the subtilisin protein. Improved calcium-free subtilisins are thus provided by the present invention.

The present invention further provides for subtilisin mutants lacking amino acids 75–83 of Sequence ID NO:1, which also have amino acids deleted in the N-terminal region (amino acids 1–22). More specifically, the present invention provides for deletions of part of all of this N-terminal region-together with further stabilizing mutations, as discussed above.

A. α-carbon plot shows the positions of mutations as noted. The numbering of wild type subtilisin is kept. Dotted spheres show the position of calcium at the weak ion binding site (B-site) and the former position of the high affinity, binding site (A-site). The A-site loop (dashed line) is absent in this mutant. N- and C-termini are indicated. The N-terminus is disordered (dotted line).

B. Close-up view of the A-site deletion., The loop from S12 subtilisin is shown as a dotted line with the continuous helix of S15. Superimposed is the 3* sigma difference electron density (FO12–FO15., phases from S15) showing the deleted A-site loop.

Figure 2:
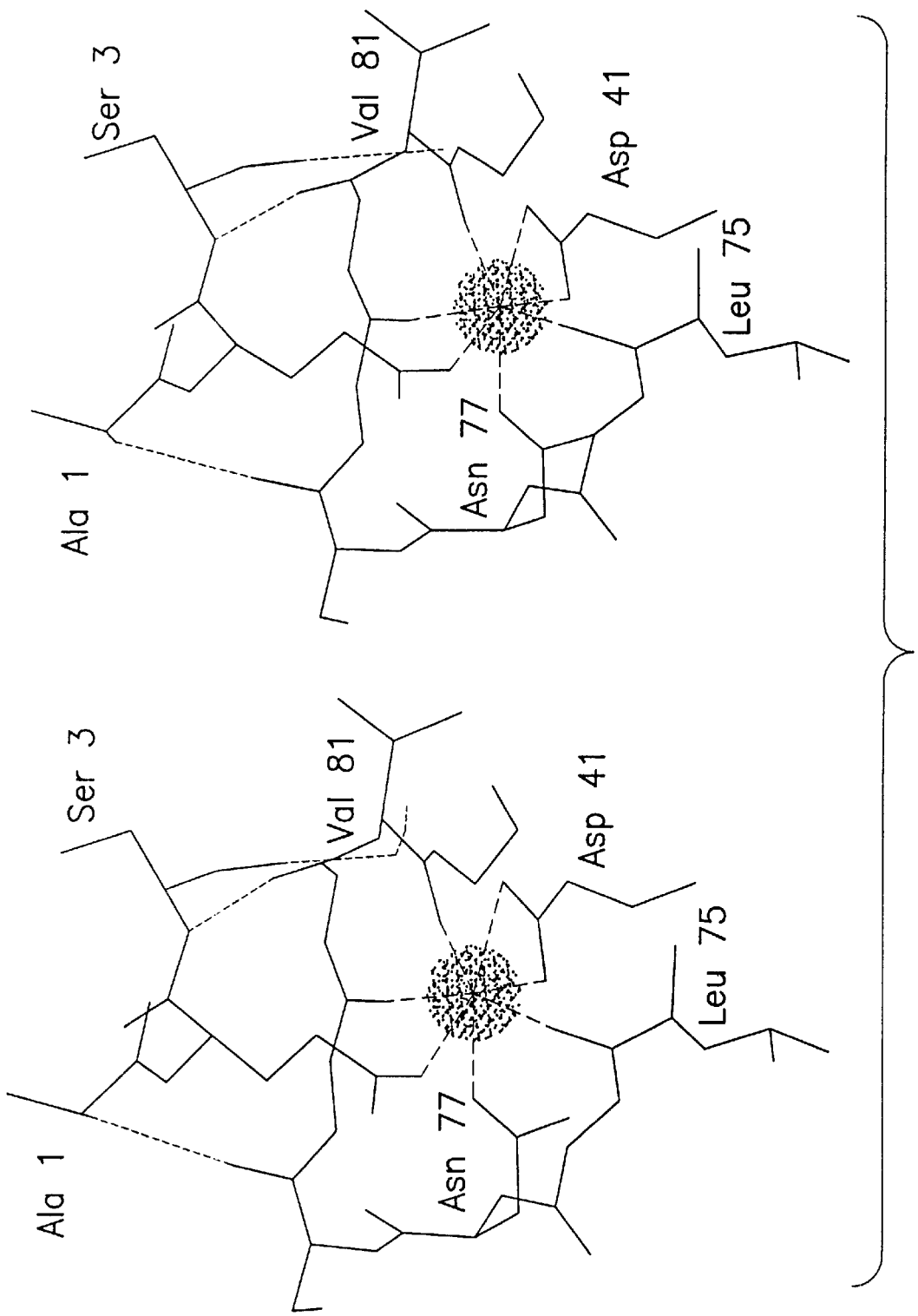

FIG. 2. X-ray crystal structure of the calcium A-site region of S12 subtilisin. Calcium is shown as a dotted sphere with one-half the van der Waals radius. Dashed lines are coordination bonds, while dotted lines represent hydrogen bonds under 3.2 Å.

Figure 3:
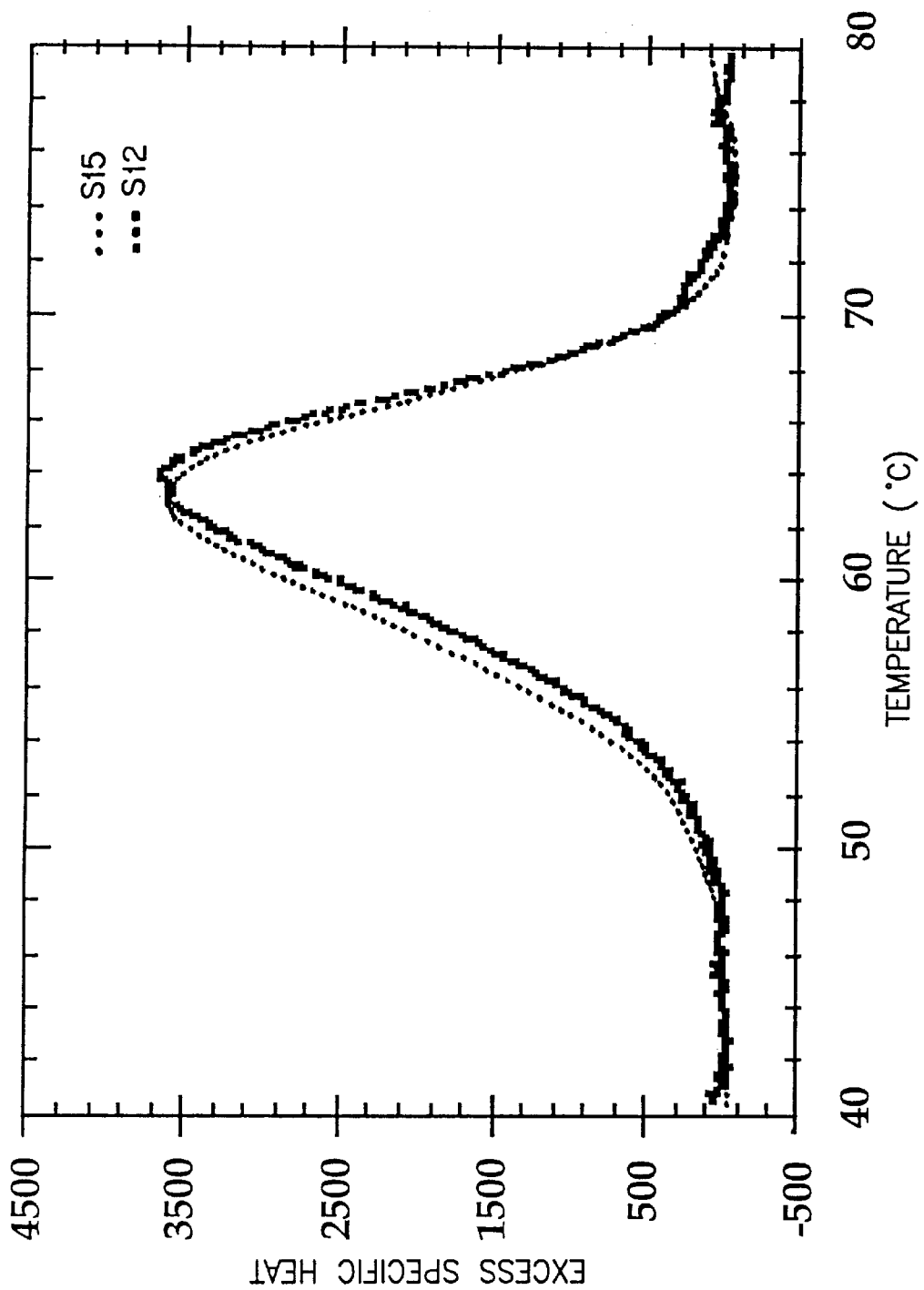

FIG. 3. Differential Scanning Caloriinetry. The calorimetric scans of apo-S12 ($T_m$=63.5° C.) and S15 ($T_m$=63.0° C.) are shown. Measurements were performed with a Hart 7707 DSC (differential scanning calorimetry) heat conduction scanning microcalorimeter as described (Pantoliano et al., Biochemistrv 28:7205–7213 (1989)). Sample conditions were 50 mM of glycine, a pH of 9.63, a scan rate of 0.5° C./min. Excess heat capacity is measured in units of $\mu J/°$. The calorimeter ampoules contained 1.78 mg of protein.

Figure 4:
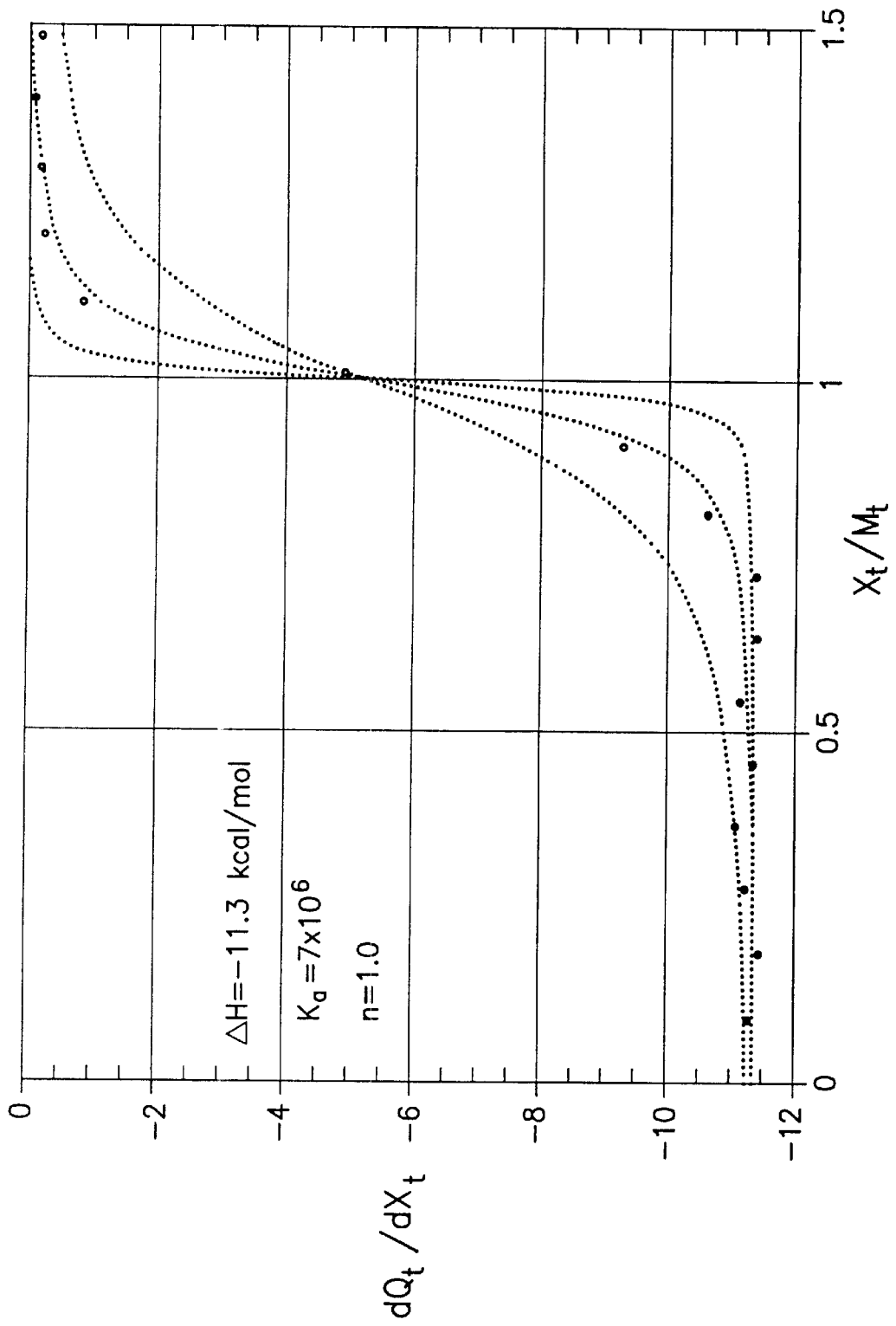

FIG. 4. Titration calorimetry of subtilisin S11. The heat of calcium binding for successive additions of calcium are plotted vs. the ratio of [Ca]/[P]. The data are best fit by a calculated binding curve assuming a binding constant of $7 \times 10^6$ and $\Delta H$ equal to 11.3 kcal/mol using equation (1) from the text. For comparison, calculated curves assuming $K_a = 1 \times 10^6$ and $1 \times 10^8$ are also shown. In this titration, [PI=100 $\mu$M and the temperature was 25° C.

FIG. 5. Kinetics of calcium dissociation from subtilisin S11 as a function of temperature. 1 $\mu$M subtilisin S11 was added to 10 $\mu$M Quin2 at time=0. Calcium dissociates from subtilisin and binds to Quin2 until a new equilibrium is achieved. The rate of calcium dissociation is followed by the increase in fluorescence of Quin2 when it binds to calcium.

A. The log of the percent of the protein bound to calcium is plotted vs. time. The kinetics of dissociation at four temperatures are shown. The dissociation follows first order kinetics for the first 25% of the reaction. As this is well before equilibrium is approached, reassociation of calcium can be neglected.

B. Temperature dependence of the rate of calcium dissociation from S15 subtilisin in the presence of excess Quin2, pH 7.4 and over a temperature range of 25–45° C. The natural log of the equilibrium constant for the transition state (calculated from the Eyring equation) is plotted vs. the reciprocal of the absolute temperature. The line is fit according to equation (3) in the text with $T_0$=298 K.

Figure 6A:
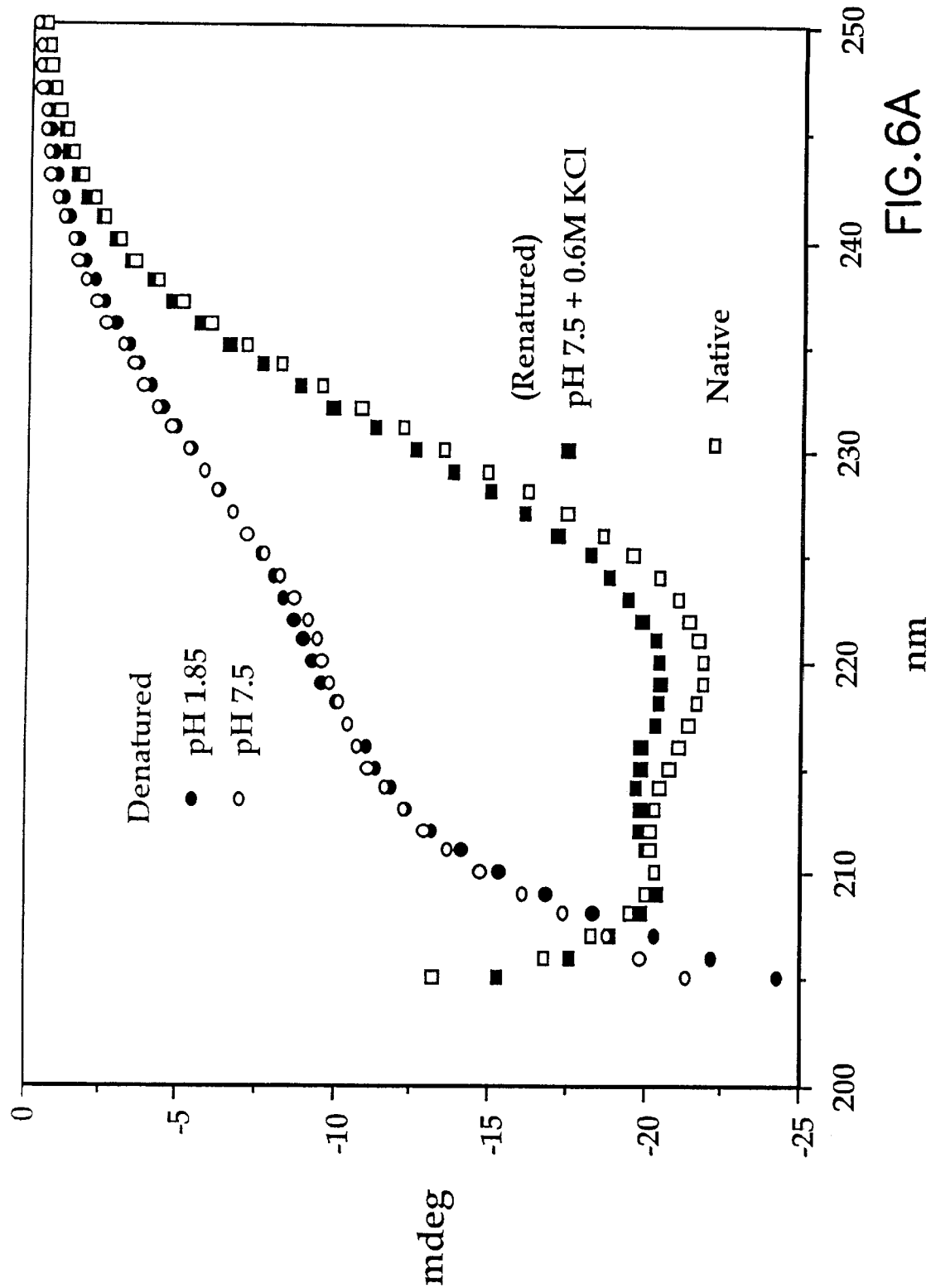

FIG. 6. Analysis of subtilisin refolding monitored by circular dichroism (CD).

A. CD spectra are shown for S15 as follows: (1) S15 in 25 mM $H_3PO_4$ at pH 1.85; (2) S15 denatured at pH 1.85 and then neutralized to pH 7.5 by the addition of NAOH; (3) S15 denatured at pH 1.85 and neutralized to pH 7.5, 30 minutes after the addition of KCI to 0.6 M; and (4) Native S15 subtilisin. Protein concentrations of all samples was 1 $\mu$M.

B. Kinetics of refolding of S15. Samples were denatured at pH 1.85 and then the pH was adjusted to 7.5. At time 0, KCI was added to the denatured protein. Recovery of native structure was followed at 222 run at KCI concentrations of 0.3 M and 0.6 M. The 0.6 M sample after 30 minutes of refolding was then used to record the corresponding spectrum in part A.

Figure 7A:
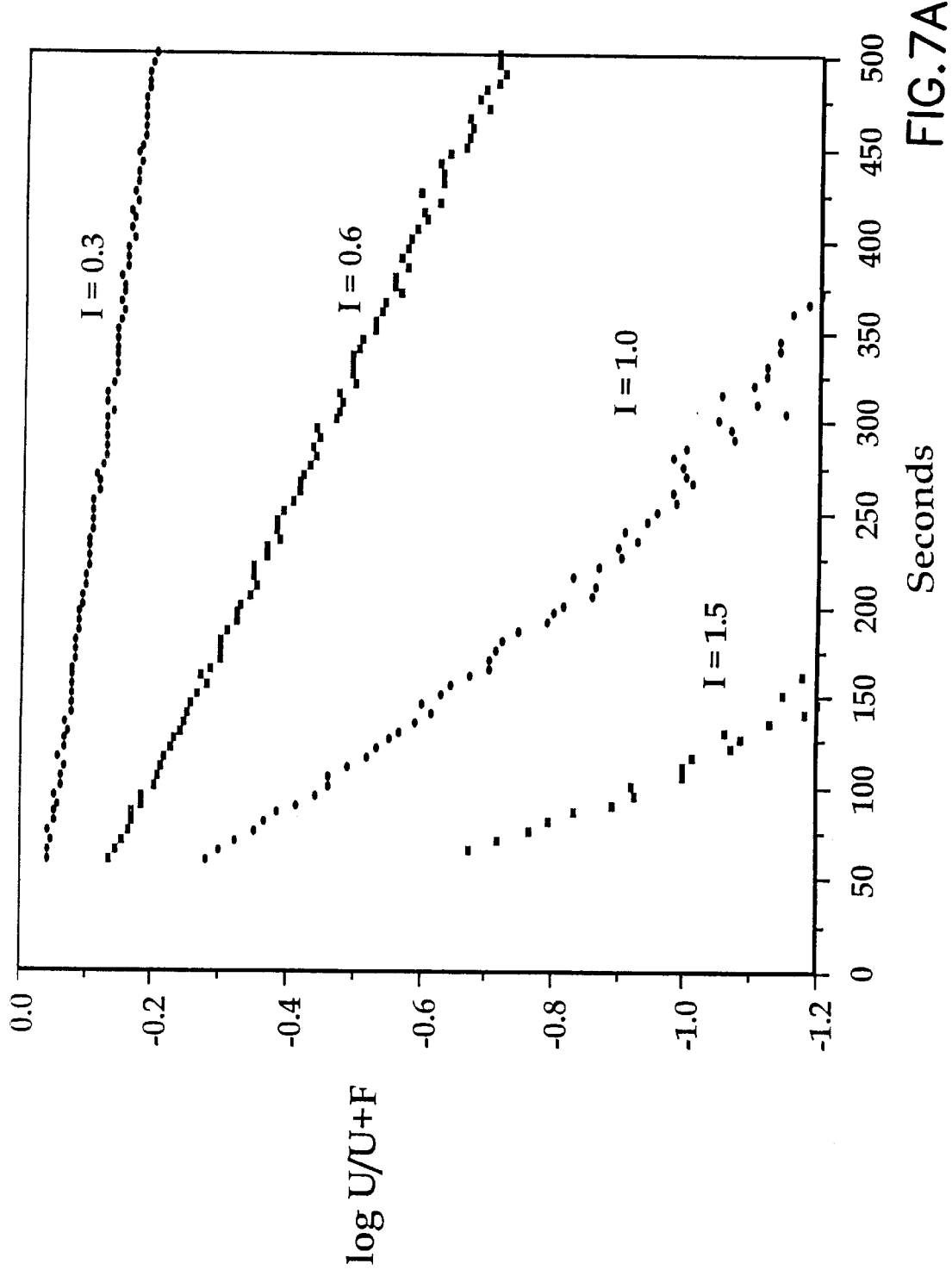
Figure 7B:
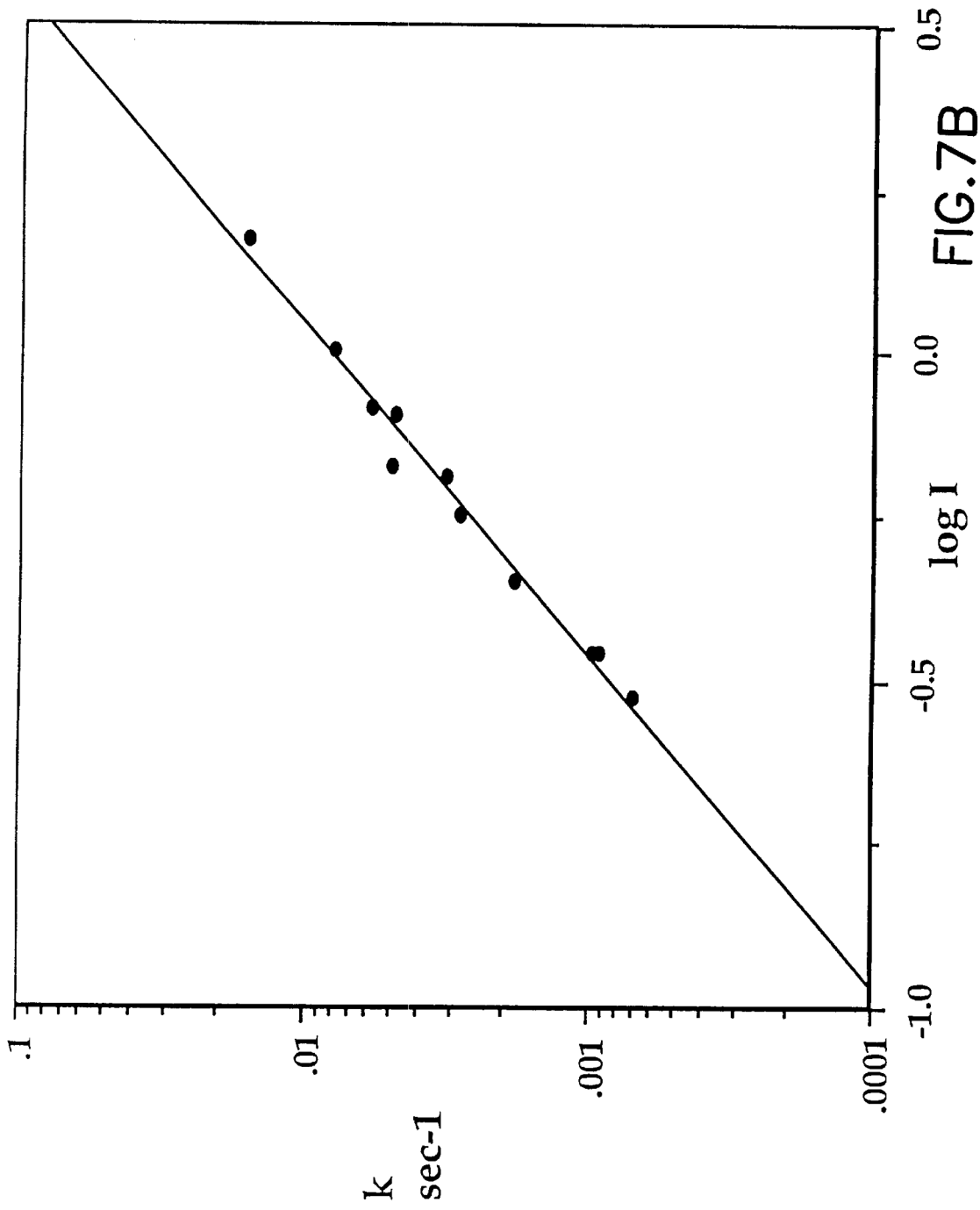

FIG. 7. Kinetics of refolding of S15 as a function of ionic strength.

A. The log of the percent unfolded protein is plotted vs. time. The kinetics of refolding are shown at four ionic strengths. The amount of refolding was determined by circular dichroism (CD) from: the increase in negative ellipticity at 222 nm. 100% folding is determined from the signal at 222 nm for native S15 at the same concentration and 0% folding is determined from the signal for acid-denatured S15. The refolding approximately follows first order kinetics for the first 90% of the reaction. Refolding was carried out at 25° C.

B. The log of first order rate constants for refolding obtained by CD or fluorescence measurements at 25° C. were plotted as a function of log of ionic strength. Ionic strength was varied from I=0.25 to I=1.5. The rate of refolding increases linearly with log I. A ten-fold increase in I results in an approximately 90-fold increase in the refolding rate.

Figure 8:
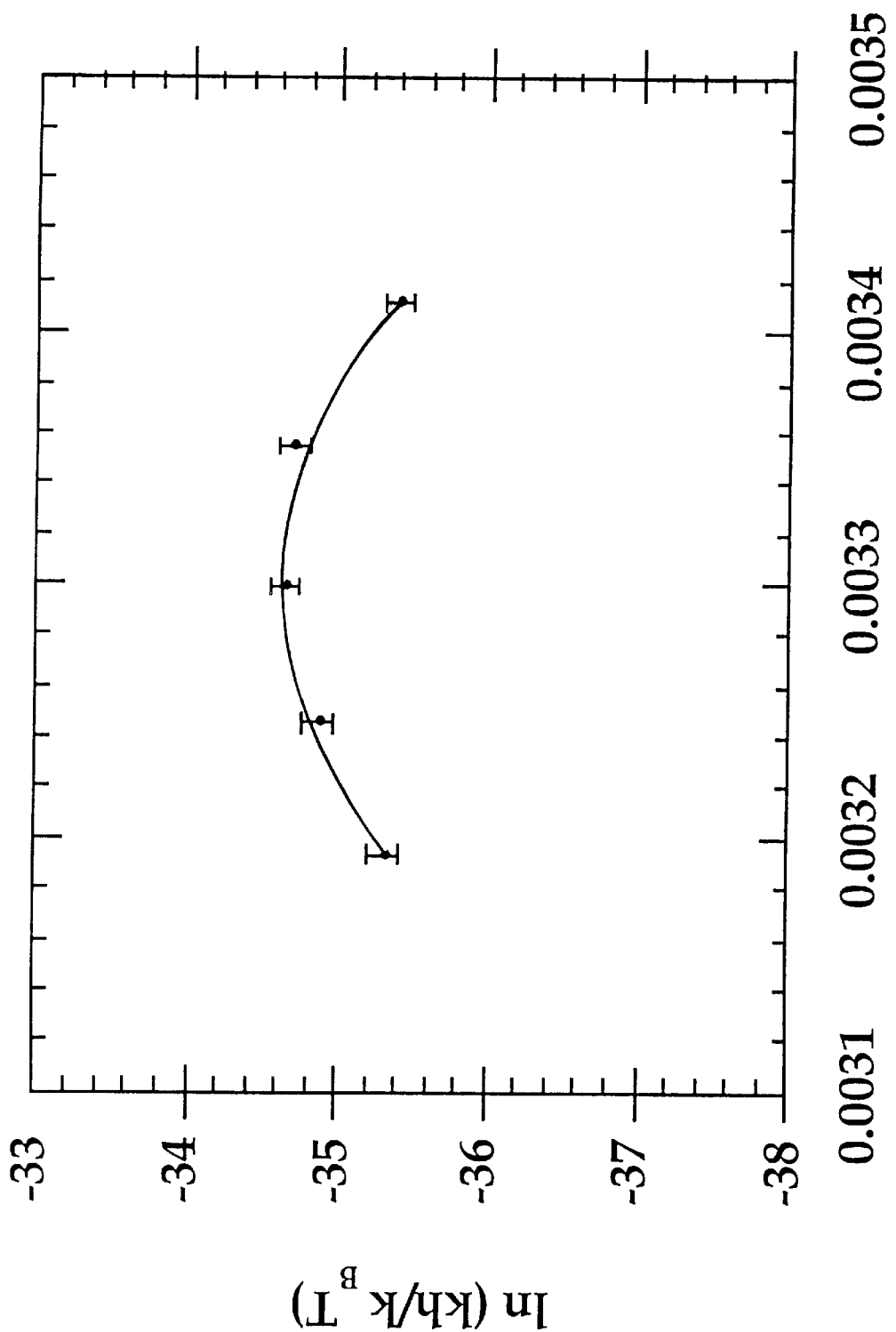

FIG. 8. Temperature dependence of the refolding rate of S15 subtilisin in 0.6 M KCl, 23 nM KP04 pH 7.3. The natural log of the equilibrium constant for the transition state (calculated from the Eyring equation) is plotted vs. the reciprocal of the absolute temperature. The line is fit according to equation 3 in the text with $T_0$=298 K.

Figure 9:
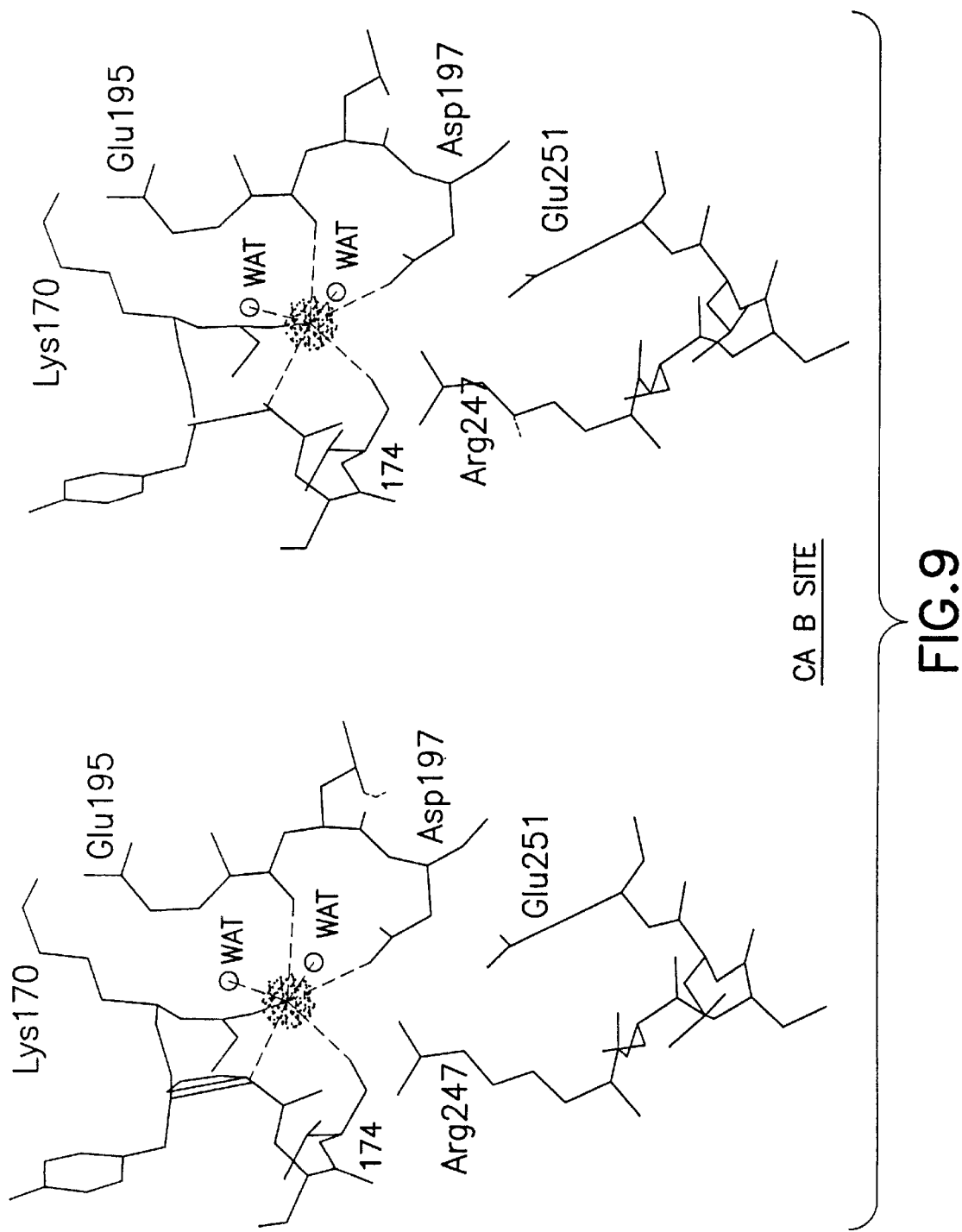

FIG. 9. X-ray crystal structure of the weak ion binding region of S15 subtilisin. Coordination bonds are shown as dashed lines. Note the preponderance of charged amino acids.

DESCRIPTION OF THE PREFERRED EMBODIMENTS

As discussed supra, calcium binding contributes substantially to the thermodynamic and kinetic-stability of extracellular microbial proteases. Moreover, with respect to subtilisin, hiah activation barriers to unfolding may be essential to retain the native conformation and to prevent transient unfolding and proteolysis given the protease-filled environment where subtilisin is secreted and as a result of auto-degradation. The unfolding reaction of subtilisin can be divided into two parts as follows:

where $N(Ca_2)$ is the native form of subtilisin with calcium bound to both sites; N(Ca) is the native form of subtilisin with calcium bound to the high affinity calcium-binding site A (Finzel et al., *J. Cell. Biochem. Suppl.* 10A:272 (1986); Pantoliano et al., *Biochemistry* 27:8311–8317 (1988); McPhalen et al., *Biochemistry* 27:6582–6598 (1988)); N is the folded protein without calcium bound; and U is the unfolded protein. The total free energy of unfolding is therefore equal to $\Delta g_1 + \Delta g_2 + \Delta g_3$. From the binding constant, one can calculate the contribution of calcium to the free energy of subtilisin folding from the following equation:

$$\Delta G_{binding} = -RT \ln(1+K_a[Ca]).$$

Thus, the contribution of site A to the stability of subtilisin in 10 mM calcium is 6.6 kcal/mol at 25° C. The contribution of calcium binding to site B in 10 mM calcium and 50 mM sodium is only 0.2 kcal/mol. This analysis is at odds with earlier studies which concluded that calcium binding to site B is responsible for the large decrease in the inactivation rate of subtilisin in the presence of millimolar concentrations of calcium (Braxton & Wells, *Biochem.* 31:7796–7801 (1992); Pantoliano et al, *Biochem.* 27: 8311–8317 (1988)).

Subtilisin is a relatively stable protein whose stability is in large part mediated by the high affinity calcium site (Voordouw et al., *Biochemistry* 15:3716–3724 (1976); Pantoliano et al., *Biochemistry* 27:8311–8317 (1988)). The melting temperature of subtilisin at pH 8.0 in the presence of μmolar concentrations of calcium is approximately 75° C. and approximately 56° C. in the presence of excess EDTA (Takehashi et al., Biochemistry 20:6185–6190 (1981); Bryan et al., *Proc. Natl. Acad. Sci. USA*, 83:3743–3745 (1986b)). Previous calorimetric studies of the calcium-free (apoenzyme, i.e., protein portion of enzyme) form of subtilisin indicated that it is of marginal stability at 25° C. with a AG of unfolding of <5 kcal/mol (Pantoliano et al., *Biochemistry* 28:7205–7213 (1989)). Because calcium is such an integral part of the subtilisin structure, the apoenzyme is thought to be a folding intermediate of subtilisin.

In order to independently examine the two phases of the folding process, the present inventors constructed a series of mutant subtilisins. First, all proteolytic activity was eliminated in order to prevent auto-degradation from occurring during the unfolding and refolding reactions. This may be accomplished, for example, by converting the active-site serine 221 to cysteine.[1] This mutation has little effect on the thermal denaturation temperature of subtilisin, but reduces peptidase activity of subtilisin by a factor of approximately $3 \times 10^4$ (Abrahmsen et al., *Biochemistry* 30:4151–4159 (1991)). This mutant, therefore, allows the folding of subtilisin to be studied without the complications of proteolysis. In the present specification, a shorthand for denoting amino acid substitutions employs the single letter amino acid code of the amino acid to be substituted, followed by the number designating where in the amino acid sequence the substitution will be made, and followed by the single letter code of the amino acid to be inserted therein. For example, S221C denotes the substitution of serine 221 to cysteine. The subtilisin mutant with this single amino acid substitution is denoted subtilisin S221C. The resulting S221C subtilisin mutant is designated S1.

[1] The S221A mutant was originally constructed for this purpose. The mature form of this mutant was heterogeneous on its N-terminus, however, presumably due to some incorrect processing of the pro-enzyme.

The subtilisin may be further mutated in order to make the relatively unstable apoenzyme easier to produce and purify. Versions of S1 with three or four additional mutations, for example, M50F, Q206I, Y217K and N218S, may also be employed in the method of the present invention. Such further mutations cumulatively increase the free energy of unfolding by 3.0 kcal/mol and increase the thermal denaturation temperature of the apoenzyme by 11.5° C. (Pantoliano et al., *Biochemistry* 28:7205–7213 (1989)). The mutant containing the M50F, Q206I, Y217K, N218S and S221C mutations is designated S11 and the mutant containing the M50F, Y217K, N218S and S221C is designated S12.[2]

[2] The specific activities of S11, S12 and S15 against the synthetic substrate, SAAPFna, are the same. (S.A.=0.0024 U/mg at 25° C., pH 8.0). These measurements were performed on protein freshly purified on a mercury affinity column.

Figure 1A:
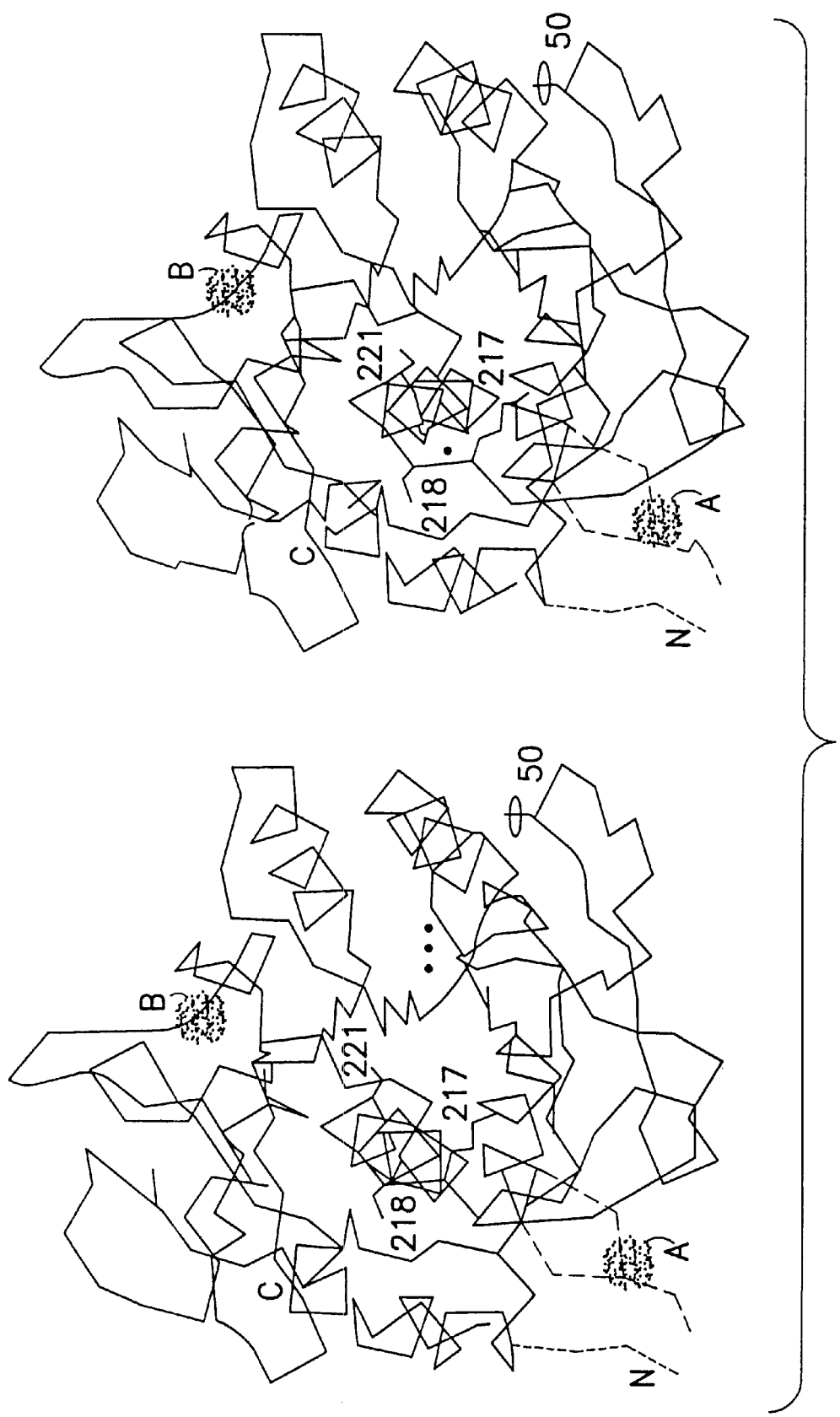
FIG. 1. X-ray Crystal structure of S15 subtilisin
Figure 1B:
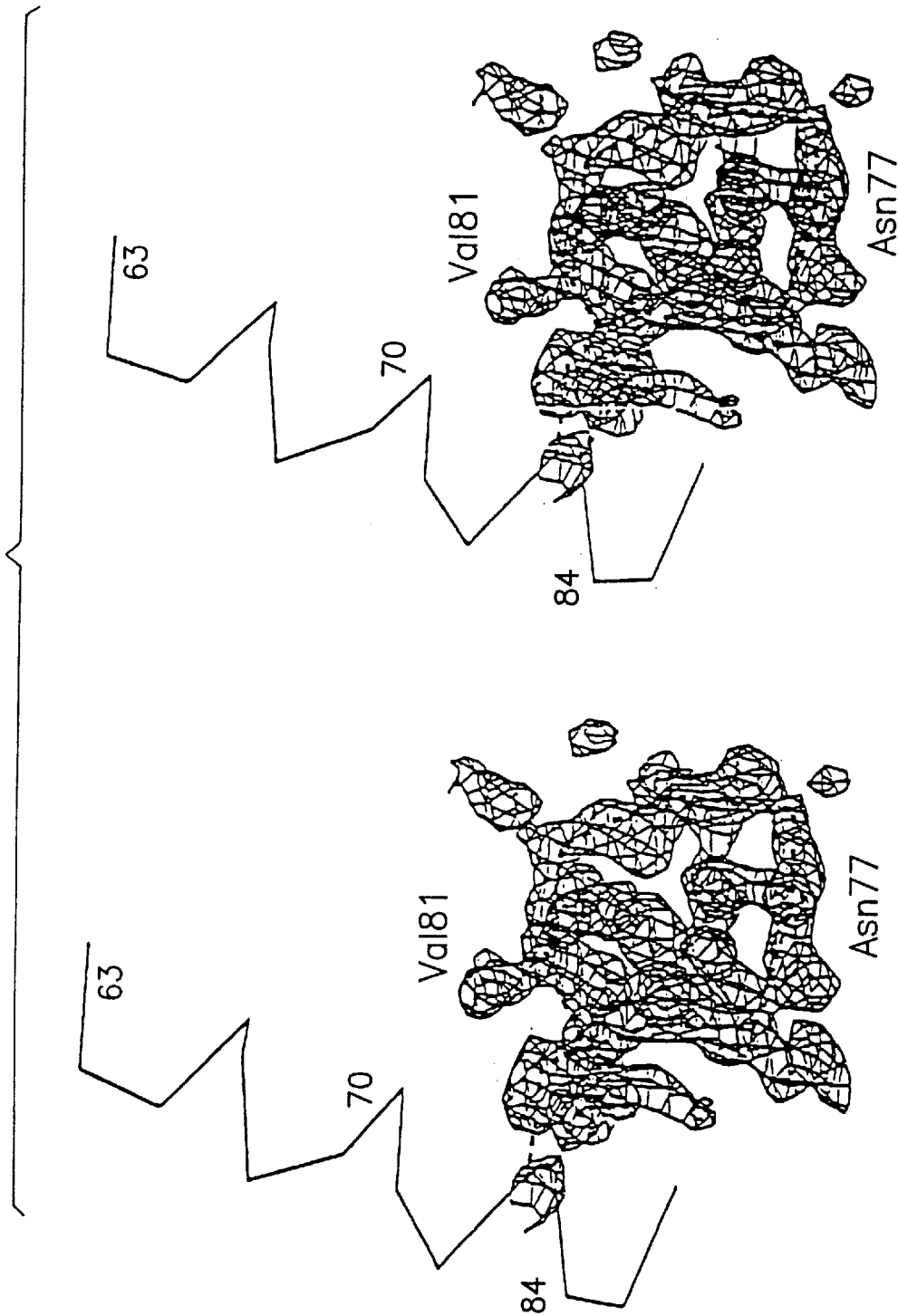

In order to produce a subtilisin BPN' protein lacking calcium binding activity, the present inventors elected to delete the binding loop in the calcium Asite to engineer a novel calcium-free subtilisin protein. This loop comprises an interruption in the subtilisin BPN' α-helix involving amino acids 63–85 of SEQUENCE ID NO:1 (McPhalen and James 1988). Residues 75–83 of the subtilisin BPN' protein form a loop which interrupts the last turn of the 14-residue alpha helix involving amino acids 63–85 [SEQUENCE ID NO: 1].[3] Four of the carbonyl oxygen licands to the calcium are provided by a loop composed of amino acids 75–83 [SEQUENCE ID NO: 1]. The geometry of the ligands is that of a pentagonal bipyramid whose axis runs through the carbonyls of amino acids 75 and 79. On one side of the loop is the bidentate carboxylate (D41), while on the other side is the N-terminus of the protein and the side chain of Q2. The seven coordination distances ran-e from 2.3 to 2.6 A, the shortest being to the aspartyl carboxylate. Three hydro-en bonds link the N-terminal seament to loop residues 78–82 in parallel-beta arrangement. A high affinity calcium binding site is a common feature of subtilisins-which make larce contributions to their high stability. By binding at specific sites in the subtilisin tertiary structure, tertiary structure, calcium contributes its binding free energy to the stability of the native state. In the present invention, site-directed mutagenesis was used to delete amino acids 75–83 of SEQUENCE ID NO: 1, which creates an uninterrupted helix and abolishes the calcium binding potential at site A (FIG. 1A and 1B).

[3] This set of nine residues was chosen for deletion, as opposed to 74–82 (those actually belonging to the loop) out of preference for Ala 74 rather than Gly 83 in the resulting continuous helix. Alanine has a higher statistical likelihood for occurrence in α-helix, due to glycine's broader range of accessible backbone conformations.

The present inventors believed that a stabilization strategy based around calcium binding would allow survival in the extracellular environment. Since the major industrial uses of subtilisins are in environments containing high concentrations of metal chelators, it was of areat practical significance for the present inventors to produce a stable subtilisin which is independent of calcium and, therefore, unaffected by the presence of metal chelating agents. Thus, stabilizing mutations in subtilisin can be classified into three groups: 1) stabilizing only in calcium, 2) stabilizing only in chelants; 3) stabilizing in both conditions (Table 1). From this partitioning it is evident that the mechanism of thermal inactivation differs depending on whether the calcium sites are occupied. To understand why this is so, one must understand how the kinetics of inactivation are related to the kinetics of unfolding and how the kinetics of unfolding are related to the kinetics of calcium loss.

While the present inventors chose to eliminate calcium binding by the removal of these amino acids (i.e. amino acids at positions 75–83), it should be possible to eliminate calcium binding by other mutations, e.g., substitution of one or more of the amino acids at positions 75–83 with alternative amino acids and by insertion, substitution and/or deletion of amino acids proximate to positions 75–83. This may also be accomplished by site-specific mutagenesis.

Additionally, because this loop is a common feature of subtilisins, it is expected that equivalent mutations for other subtilisins, in particular class I subtilases, e.g., by site-specific mutagenesis, will likewise eliminate calcium binding and provide for enzymatically active mutants.

In particular, the present inventors synthesized by site-specific mutagenesis three subtilisin BPN' DNA's which have been mutated to eliminate amino acids 75–83 involved in calcium binding and which further comprise additional substitution mutations. These mutated subtilisin BPN' DNA's, upon expression of the DNA, provide for subtilisin proteins having enhanced thermal stability and/or which are resistant to proteolysis.

The specific subtilisin BPN' mutants synthesized by the present inventors are designated in this application as S15, S39, S46, S47, S68, S73, S79, S86, S88 and pS149. The specific point mutations set forth in the present application identify the particular amino acids in the subtilisin BPN' amino acid sequence, as set forth in SEQUENCE ID NO: 1, that are mutated in accordance with the present invention. For example, the S15 mutant comprises a deletion of amino acids 7583 and additionally comprises the following substitution mutations: S221C, N218S, M50F and Y217K. The S39 mutant similarly comprises a deletion of amino acids 75–83 and additionally comprises the following substitution mutations: S221C, PSA, N218S, M50F and Y217K. The S46 mutant comprises a deletion of amino acids 75–83 and additionally, comprises the following substitution mutations: M50F, Y217K and N218S. The S47 mutant similarly comprises a deletion of amino acids 75–83 and additionally comprises the following substitution mutations: P5A, N218S, M50F and Y217K. The S68 mutant comprises a deletion of amino acids 75–83 and additionally comprises the following substitution mutations: P5S, N218S, M50F and Y217K. The S73 mutant comprises a deletion of amino acids 75–83 as well as the following substitution mutations: Q2K, M50F, A73L, Q206V, Y217K and N218S. The S79 mutant comprises a deletion of amino acids 75–83 and additional comprises the following substitution mutations: Q2K, M50F, A73L, Q206C, Y217K and N218S,. The S86 mutant comprises a deletion of amino acids 75–83 as well as the following substitution mutations: Q2K, S3C, M50F, A73L, Q206C, Y217K and N218S. The S88 mutant comprises a deletion of amino acids 75–83 as well as the following substitution mutations: Q2K, S3C, P5S, K43N, M50F, A73L, Q206C, Y217K, N218S, and Q271E. Finally, the pS149 mutant comprises a deletion of amino acids 75–83 as well as the mutations present in the S88 mutant and the following substitution mutations: S9A, I31L, E156S, G166S, G169A, S188P, N212G, K217L and T254A. The specific activities of the proteolytically active S46, S47, S68, S73, S79, S86, S88 and pS149 subtilisins have been found to be similar or enhanced in relation to the wild-type enzyme.

The inventors also consider as part of their invention Δ75–83 subtilisin mutants which contain one or more of the following mutations: Q2K, S3C, P5S, K43N, M50F, A73L, Q206C, Y217K, N218S, Q271E, S9A, I31L, E156S, G166S, G169A, S188P, N212G, K217L and T254A. Furthermore, applicants consider as part of their invention Δ75–83 subtilisin mutants which contain one or more substitutions selected from the group consisting of S9A, I31L, E156S, G166S, G169A, S188P, N212G, K217L, L1261, M222Q and T254A, and optionally together with at least one or more substitutions selected from the group consisting of Q2K, S3C, P5S, K43N, M50F, A73L, Q206C, Y217K, N218S, and Q271E.

The inventors further consider to be part of their invention Δ75–83 subtilisin mutants which have a part or all of the N-terminal region deleted (aa 1–22). An example of such a mutant subtilisin protein is S176, which has the Δ75–83 deletion and a deletion of amino acids 1–22. Another example of such a mutant subtilisin protein is S177, which has the Δ75–83 deletion as well as a deletion of amino acids 1–17. One of skill in the art could easily determine other deletions within the N-terminal region which could be made to the subtilisin mutant proteins of the present invention. Such mutations should preserve the structural integrity and stability of the subtilisin protein. One of skill in the art could determine which mutations within the N-terminal region are preferable by measuring the stability and structural integrity of the mutant using technologies such as circular dichroism.

These mutant subtilisins (with the Δ75–83 deletion and the deletion of part or all of the N-terminal region) may also have any of the stabilizing mutations discussed above (i.e. S221C, Y217K, P5A, M50F, N218S, P5S, Q2K, A73L, Q206V, Q206C, S3C, K43N, Q271E, S9A, I31L, E156S, G166S, G169A, S188P, N212G, K217L, T254A, L1261 and M222Q). Most preferably, the stabilizing mutations are present in the following amino acid positions: 41–45; 70–74; 86–87; 181–184; 200–214; 226–237; and 267–275.

The various Δ75–83 subtilisins which were synthesized by the inventors are shown in Tables 1 and 2, below. The particular points of mutation in the amino acid sequence of subtilisin BPN' amino acid sequence, as set forth in SEQUENCE ID NO:1, are identified. The synthesis of these mutants is described in more detail infra.

ence of metal chelators, it is disadvantageous in at least one respect. Specifically, the elimination of the calcium loop without any other compensating mutations results in the destabilization of the native state relative to the partially folded states and, therefore, a loss of cooperativity in folding. The present inventors thus sought to further geneti-

TABLE I

Subtilisin Mutations

|  | S221C | P5A | Δ75–83 | N218S | M50F | Q2061 | Y217K | Q271E | Q2K | A73L | K43N | Q206C | S3C |
|---|---|---|---|---|---|---|---|---|---|---|---|---|---|
| BPN' | − | − | − | − | − | − | − | − | − | − | − | − | − |
| S1* | + | − | − | − | − | − | − | − | − | − | − | − | − |
| S11* | + | − | − | + | + | + | + | − | − | − | − | − | − |
| S12* | + | − | − | + | + | − | + | − | − | − | − | − | − |
| S15* | + | − | + | + | + | − | + | − | − | − | − | − | − |
| S39 | + | + | + | + | + | − | + | − | − | − | − | − | − |
| S46 | − | − | + | + | + | − | + | − | − | − | − | − | − |
| S47 | − | + | + | + | + | − | + | − | − | − | − | − | − |
| S68 | − | P5S | + | + | + | − | + | − | − | − | − | − | − |
| S73 | − | − | + | + | + | − | + | − | − | − | − | − | − |
| S79 | − | − | + | + | + | − | + | + | + | + | − | + | − |
| S86 | − | − | + | + | + | − | + | + | + | + | − | + | + |
| S88 | − | P5S | + | + | + | − | + | + | + | + | + | + | + |

The plus signs show that a subtilisin contains a particular mutation. X-ray crystal structure of wild type, S12 and S15 have been determined to 1.8Å.
*S1, S11, S12, S15 and S39 are low activity mutants constructed to aid in the evaluaton of structure and conformational stability.

|  | S88 | S9A | 131L | E156S | G166S | G169A | N212G | S188P | K217L | T254A |
|---|---|---|---|---|---|---|---|---|---|---|
| pS149* | 88 | + | + | + | + | + | + | + | + | + |

*pS149 contains all of the mutations present in S88, in addition to the mutations depicted in the table.

In order to understand the contribution of calcium binding to the stability of subtilisin, the thermodynamics and kinetics of calcium binding to the high affinity calcium A-site were measured by microcalorimetry and fluorescence spectroscopy. Calcium binding is an enthalpically driven process with an association constant ($K_a$) equal to $7 \times 10^6$ M$^{-1}$. The kinetic barrier to calcium removal from the A-site (23 kcal/mol) is substantially larger than the standard free energy of binding (9.3 kcal/mol). The kinetics of calcium dissociation from subtilisin (e.g, in excess EDTA) are accordingly very slow. For example, the half-life ($t_{1/2}$) of calcium dissociation from subtilisin, i.e., the time for half of the calcium to dissociate from subtilisin, is 1.3 hours at 25° C.

X-ray crystallography shows that except for the region of the deleted calcium-binding loop, the structure of the subtilisin mutants and the wild type protein are very similar. The N-terminus of the wild-type protein lies beside the site A loop and furnishes one calcium coordination ligand, the side chain oxygen of Q2. In Δ5–83 subtilisin, the loop is -one, leaving residues 1–4 disordered. These first four residues are disordered in the X-ray structure since all its interactions were with the calcium loop. N-terminal sequencing confirms the first four amino acids are pesent, confirming that processing occurs at the normal site. The helix is shown to be uninterrupted and shows normal helical geometry over its entire length. X-ray crystallography further shows that the structures of subtilisin with and without the deletion superimpose with a root mean square (r. m. s.) difference between 261 α-carbon positions of 0.17 Å and are remarkably similar considering the size of the deletion. Diffuse difference density and higher temperature factors, however, indicate some disorder in the newly exposed residues adjacent to the deletion.

While the elimination of calcium binding is advantageous since it produces proteins that are more stable in the prescally engineer the subtilisin S15 BPN' protein lacking amino acids 75–83 in order to restore cooperativity to the folding reaction. In most well designed proteins all parts of the molecule are interdependent, making the unfolding reaction highly cooperative. Cooperativity of the folding reaction allows proteins to achieve sufficient stabilities of the native state for proper function since the overall stability of the native conformation is roughly the sum of all local interactions.

Therefore, while the Δ75–83 subtilisin is an example of an engineered subtilisin which is active and stable in the absence of calcium, the present inventors sought to improve this protein by further mutation. The design of a particular highly stable calciwn-free subtilisin relies on an iterative engineering cycle. The present inventors found that the requisite first step in the cycle was to greatly diminish the proteolytic activity of subtilisin. This is necessary because calcium contributes greatly to the conformational stability of subtilisin and the early versions of calcium-free subtilisin are susceptible to proteolysis. After reducing the susceptibility to proteolysis, the next step in the cycle was to eliminate sequences essential for calcium binding, i.e., the A-site. Although the S15 Δ75–83 subtilisin is much less stable than the wild type subtilisin in the presence of calcium, this mutant is more stable than wild type subtilisin in the presence of the metal chelator EDTA.

Accordingly, the third step was to improve the stability of the calciumfree subtilisin protein. To improve the stability of calcium-free subtilisin, the present inventors next tried to create a home for the disordered N-tenninal residues. In order to create a highly stable calcium-free subtilisin, the N-terminal part of the protein which is destabilized by the deletion of the calcium A-loop may be modified. For example, the N-terminus which is disordered may be deleted or extended. This, however, is problematic because the requirements for processing the propeptide from the mature protein are not known. It is known, however, that the processing site is not determined by amino acid sequence since mutants Y1A (the C-terminus of the propeptide), A1C and Q2R do not alter the site of cleavage. It is also known that the native structure of the N-terminus in subtilisin does not determine the cleavage site because the A75–83 variants are processed correctly. Since it is not yet known how to alter the processing site, interactions with the existing N-terminus may be optimized.

Examination of the structure of S15 subtilisin revealed numerous possibilities for improving stability of the mutant enzyme. The regions of the structure most affected by the deletion are the N-terminal amino acids 1–8, the 36–45 ω-loop, the 70–74 α-helix the 84–89 helix turn and the 202–219 β-ribbon. As previously stated, the first four residues in Δ75–83 subtilisin are disordered in the x-ray structure since all its interactions had been with the calcium loop. N-terminal sequencing shows, however, that the first four amino acids are present confirming that processing occurs at the normal site. Other than the N-terminus, there are three other residues whose side chain conformations are distinctly different from wild type. Y6 swings out of a surface niche into a more solvent-exposed position, as an indirect effect of the destabilization of the N-terminus. D41, a former calcium ligand, and Y214 undergo a coordinated rearrangement, forming a new hydrogen bond. The B-factors of all three residues increase significantly due to the deletion of amino acids 75–83. In addition, S87 and A88 do not change conformation but exhibit significantly increased B-factors. P86 terminates the a-hela from which the calcium loop was deleted. In view of the above, other mutations at one or more of the above mentioned sites, or at the amino acids proximate thereto, will provide for subtilisin BPN' mutants comprising greater enzymatic activity or increased stability.

There are several logical strategies for remodeling this region of the protein to produce subtilisin BPN' mutants comprising greater enzymatic activity or increased stability. Since the N-terininal four amino acids are disordered in the x-ray structure, one possible approach would be to delete them from the protein. The requirements for processing the propeptide from the mature protein are not understood, however. Inserting or deleting amino acids from the N-terminal region is, therefore, problematic. For this reason possible to increase the stability of the molecule by substituting, deleting or adding at least one amino acid at positions whose environment was changed by the 75–83 deletion.

The first attempt was to mutate the proline at position 5 to alanine to create more flexibility at position 5. This increased flexibility allows the N-terminus to try to find a unique position along the new surface of the protein, created by deletion of the calcium loop. Once the N-terminus assumes a unique location its local interactions may then be optimized.

The P5A mutation was made to try to create more flexibility for the N-terminus and allow it to find a unique position along the new surface of the protein that was created by deletion of the calcium loop. In the native structure, the first five amino acids are in an extended conformation and form β-pair hydrogen bonds with the calcium loop as well as the Q2 side chain interaction with the calcium. The proline at position 5, which is conserved among seven bacterial subtilisins which have a homologous calcium A-site, may help stabilize the extended conformation. The P5A mutation in Δ75–83 subtilisin should thus result in an increase in the cooperativity of the unfolding reaction. The X-ray structure'of this variant has been determined to 1.8 Å.

In toto, the present inventors selected amino acids at ten different positions whose environment had changed substantially for substitution. A mutagenesis and screening procedure was developed in order to screen all possible substitutions at a particular site. The technique for generating and screening subtilisin variants involves in vitro mutagenesis of the cloned subtilisin gene, expression of the mutated genes in *B. subtilis*, and screening for enhanced stability.

For example, site-directed mutagenesis was performed on the S46 subtilisin gene using oligonucleotides which were degenerate at one codon. The degenerate codon contained all combinations of the sequence NNB, where N is any of the four nucleotides and B is T, C or G. The 48 codons represented in this population encode for all twenty amino acids but exclude the ochre and umber termination codons. The mutagenized genes were used to transform *B. subtilis*. Examples of particular mutations are shown in Table II as follows:

TABLE II

Site-directed mutagenesis

| Region of protein | Site | Stabilizing mutations | Mutagenic Oligonucleotide |
|---|---|---|---|
| N-terminus | Q2 | K, W, L | AC GCG TAC GCG NNB TCC GTG CCT TAC |
| | S3 | C* | GCG TAC GCG AAG MMB GTG CCT TAC CG |
| | V4 | none | C GCG AAG TCC NNB CCT TAC GGC G |
| | P5 | S | CAG TCC GTG NNB TAC GGC GTA TC |
| 36–44 omega loop | D41 | A | GAT TCT TCT CAT CCT NNB TTA AAG GTA GC |
| | K43 | R, N | CAT CCT GAT TTA NNB GTA GCA GGC GG |
| 63–85 α-helix | A73 | L, Q | GGC AVA GTT NNB GCT GTT GCG |
| | A74 | none | C ACA GTT GCG NNB GTT GCG CCA AG |
| 202–220 β-ribbon | Q206 | I, V, W, C* | C GTA TCT ATC MMB AGC ACG CTT CC |
| | Y214 | none | CCT GGA AAC AAA NTN GGG GCG AAA TC |

*Double cysteine mutations at positions 3 and 206 have been found to be as stabilizing as a disulfide bond.

insertions and deletions in the N-terminal region were avoided in favor of amino acid substitutions. Many of the original amino acids in the above described regions of subtilisin which interacted with the amino acids 75–83 loop can be assumed to no longer be optimal. It was, therefore, To have a 98% chance of finding tryptophan, glutamine, glutamate or methionine in the mutant population, one must screen about 200 mutant clones. Each of those codons is represented by only one of the 48 codons contained in the population of sequences NNB. Codons for all other amino acids are represented by at least two codons in the population and would require screening of about 100 mutant clones to have a 98% chance of being represented in the mutant population.

To identify the optimum amino acid at a position, mutants were screened for retention of enzymatic activity at high temperature. 100 tLI of media was dispensed in each of the 96 wells of a microliter dish. Each well was inoculated with a Bacillus transformant and incubated at 37' with shaking. After 18 hours of growth, 20 µl of culture was diluted into 80 µl of 100 mM Tris-HCI, pH 8.0 in a second microliter dish. This dish was then incubated for one hour at 65° C. The dish was allowed to cool to room temperature following the high temperature incubation and 100 µl of 1 mM SAAPF-pNA was added to each well. The wells which cleaved the pNA (turned yellow) quickest were deemed to contain the most heat resistant subtilisin mutant. Once preliminary identification of a stable mutant was made from the second microliter dish, the Bacillus clone in the corresponding well in the first microliter dish was grown up for further analysis.

The screening procedure identified stabilizing mutations at seven of the ten positions which were examined. As noted, these amino acid positions were selected at positions of the protein whose envirorunent has changed substantially by virtue of the calcium domain deletion. No mutations were identified at positions 4, 74 and 214 which by themselves significantly increased the half-life of the mutant relative to the parent subtilisin. However, at position 214 the effect of only hydrophobic amino acids was screened. No mutations were found at positions 5, 41 and 43 which resulted in measurable but modest increases in stability. Moreover, several mutations were found at positions at 2, 3, 73, and 206 which significantly increased the half-life of the mutant relative to the parent subtilisin. These stabilizing mutations are shown in Table III as follows:

TABLE III

Stabilizing Mutations

| Region of protein | Site | Increase |
|---|---|---|
| N-terminus: | Q2K | 2.0-fold |
| 63–85 α-helix: | A73L | 2.6-fold |
| 202–220 β-ribbon | Q206V | 4.5-fold |
| N-tenninus-β-ribbon | S3C-Q206C (disulfide) | 14-fold |

Stabilizing amino acid modifications at positions 2(K), 73(L) and 206(V) were then combined to create subtilisin S73. The properties of S73 subtilisin as well as S46, S79 and S86 are summarized in Table IV.

TABLE IV

| Mutant | Mutations[1] | Specific activity[2] | Half-life (60 C)[3] | Increase |
|---|---|---|---|---|
| S46 | — | 100 U/mg | 2.3 min | |
| S73 | Q2K A73L Q206V | 160 U/mg | 25 min | 11-fold |
| S79 | Q2K A73L Q206C | N.D.[4] | 18 min | 8-fold |
| S86 | Q2K, S3C[5] A73L Q206C[5] | 85 U/mg | 80 min | 35-fold |

[1]All of subtilisins S46, S73, S79 and S86 contain the mutations M50F, Y217K and N218S and Q271E.

TABLE IV-continued

| Mutant | Mutations[1] | Specific activity[2] | Half-life (60 C)[3] | Increase |
|---|---|---|---|---|

[2]Specific activity is measured against succinyl-L-Ala-L-Ala-L-Pro-L-Phe-p-nitroanilide(SAAPF-pNA) in 10 mM Tris-HCl, pH 8.0 at 25'C.
[3]Half-life is measured at 60'C in 10 mM Tris-HCI, pH 8.0 50 mM NaCl and 10 mM EDTA.
[4]Not determined.
[5]Disulfide bond was formed between the cysteines at positions 3 and 206. The fomiation of a disulfide bond was confirmed by measuring the radius of gyration of the denatured protein by gel electrophoresis.

In many cases, the choice of amino acid at a particular position will be influenced by the amino acids at neighboring positions. Therefore, in order to find the best combinations of stabilizing amino acids, it will be necessary in some cases to vary the amino acids at two or more-positions simultaneously. In particular, this was effected at positions 3 and 206 with amino acids whose side chains can potentially interact. It was determined that the best combination of modifications was cysteine modifications at positions 3 and 206. This modification was denoted as S86. Because of the close proximity and suitable geometry between the cysteines at these two positions a disulfide cross-link forms spontaneously between these two residues.

The stability of the S86 subtilisin was studied in relation to S73. It was found that the half-life of S86 is 80 minutes at 60° C. in 10 mM Tris-HCl, pH 8–0, 50 mM NaCl and 10 mM EDTA, a 3.2-fold enhancement relative to S73 subtilisin. By contrast, a 3–206 disulfide cross-link would not be able to form in native subtilisins which contain the calcium A-site because the 75–83 binding loop separates the N-terminal amino acids from the 202–219 B ribbon. Therefore, the enhancement in stability which occurs in the subject S86 mutant lacking the 75–83 binding loop will likely not be observed with native subtilisins similarly cysteine modified at these positions.

It is expected that similar enhancement in stability will be inherent to other subtilisins of the I-S1 and I-S2 group if their calcium loops were deleted (see Siezen et al, *Protein Enizineering*, 4, pp. 719–737 at FIG. 7). This is a reasonable expectation based on the fact that the primary calcium site in these different. subtilisins are formed from almost identical 9 residue loops comprised in the identical position of helix C.

X-ray structures of the I-S1 subtilisins BPN and Carlsberg, as well as the I-S2 subtilisin (savinase), have been determined to high resolution. Comparison of these structures demonstrates that all three have almost identical calcium A-sites.

The x-ray structure of the class I subtilase, thermitase from *Thermoactinomyces vulgaris*, is also known. Though the overall homology of BPN' to thermitase is much lower than the homology of BPN' to I-S1 and I-S2 subtilisins, therrnitase has been shown to have an analogous calcium A-site. In the case of thermitase, the loop is a ten residue interruption at the identical site in helix C.

Thus, it is expected that the stabilizing mutations exemplified herein will impart similar beneficial effects on stability for the calcium loop-deleted versions of other class I subtilases.

The stability of S73, S76 and S86 subtilisins relative to S46 subtilisin was compared by measuring their resistance to thermal inactivation at 60° C. in 10 mM Tris-HCI, pH 8.0, 50 mM NaCl and 10 mM EDTA. Aliquots were removed at intervals and the activity remaining in each aliquot was determined. Under these conditions, the half-life of S46 subtilisin is 2.3 minutes and the half-life of S73 is 25 minutes (Table IV).

In order to identify other mutants having increased stability any mutagenesis technique known by those skilled in the art may be used. One example of such a technique for generating and screening subtilisin variants involves three steps: 1) in vitro mutagenesis of the cloned subtilisin gene; 2) expression of mutated genes in *B. subtilis*, and 3) screening for enhanced stability. The key element in the random mutagenesis approach is being able to screen large numbers of variants.

Although random mutagenesis may be employed, the mutagenesis procedure described above allows for mutations to be directed to localized regions of the protein (e.g., the N-terminal region). As noted supra, the S46, S47, S68, S73, S79 and S86 mutants (which comprise the active-site S221) were found to be enzymatically active. It is expected that other substitutions may be identified which provide for equivalent or even greater stability and activity.

The activities of examples of the calcium-free subtilisin mutants of the present invention against the substrate sAAPF-pNA in Tris-HCl, pH 8.0 and 25° C. are given in Table V as follows:

TABLE V

| Subtilisin | Specific activity | Half-life (55° C.) |
|---|---|---|
| BPN' | 80 U/mg | 2 min |
| S12 | 0.0025 U/mg | N.D.[1] |
| S15 | 0.0025 U/mg | N.D.[1] |
| S39 | 0.0025 U/mg | N.D.[1] |
| S46 | 125 U/mg | 22 min |
| S47 | 90 U/mg | 4.7 min |
| S68 | ~100 U/mg | 25 min |

[1]Half-lives were not determined for inactive subtilisins.

As shown above, the subtilisin mutants S46, S47, S68, S73, S79 and S86 have enhanced catalytic activity in comparison with subtilisin BPN'. Changes in catalytic efficiency due to the deletion were not expected because of the fact that the active site of subtilisin is spatially distant from the calcium A-site.

The stability of these mutant subtilisins was compared to native subtilisin BPN' by measuring their resistance to thermal inactivation. Since the stability of the calcium-free subtilisin mutants should be unaffected by metal chelating agents, the experiment was carried out in EDTA. Thermal inactivation in EDTA is a two step process as shown in the following mechanism:

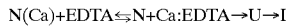

The rate of calcium dissociation with the rate of unfolding as a function of temperature for an inactive variant of subtilisin BPN' was compared in Bryan et al (*Biochem.* 31:49374945 (1992)). Repartitioning of calcium from site A into a strong chelator occurs at a rate 5 hour $^{-1}$ at 45° C. The kinetic barrier to calcium removal is 23 kcal/mol. Calcium is a integral part of the subtilisin structure and its association or dissociation requires significant but transient disruption in surrounding protein-protein interactions. This disruption in structure would explain the high activation energy and slow kinetics of calcium binding and dissociation. For example, breaking main-chain hydrogen bonds between the N-terminal region and the 75–83 loop region would allow the relatively buried calcium a passageway into or out of the protein. Global unfolding in 10 M EDTA at 45° C. is much slower than calcium dissociation, however, occurring at a rate of 0.04 hour $^{-1}$, with an activation energy of ~60 kcal/mol. Thus the predominant mechanism of inactivation in EDTA is calcium dissociation followed by unfolding and loss of activity.

Because calcium binding reaches equilibrium quickly relative to the rate of unfolding, mutations which stabilize in EDTA must stabilize apo-subtilisin. Increasing the binding constant for one of the calcium sites would not help unless the increase in binding affinity were enormous. Consider a typical experiment in which 1 mM EDTA is added to 100 µg/ml subtilisin (3.6 µM) bound to a stoichiometric amount of calcium. The calcium will partition between subtilisin and EDTA according to the equation:

$$[SCa]/[S_{total}]=K_{S-Ca}[S]/(1+K_{S-Ca}[S]+K_{E-Ca}[E])$$

where $[SCa]/[S_{total}]$ is the fraction of subtilisin bound to calcium, [S]~total subtilisin and [E]~total EDTA. Since the binding constant of subtilisin for calcium at site A ($K_{S-Ca}$)= $7 \times 10^6$ M$^{-1}$ and the binding constant of EDTA for calcium ($K_{E-Ca}$)=$2 \times 10^8$ M$^{-1}$, then less than 0.02% subtilisin would be bound to calcium at equilibrium. Examples of mutations which stabilize apo-subtilisin are M50F and the disulfides C22–C87 and C206–C216 (Pantoliano et al, *Biochem.* 28:7205–7213 (1989)). The irony is that a mutation which preferentially stabilizes apo-subtilisin relative to the bound form, will weaken calcium binding and catalyze inactivation under conditions of excess calcium and high temperature (see the mechanism below). This phenomenon is displayed in the M50F mutant, which is more stable than wild type in 10 mM EDTA but less stable in 10 mM CaCl$_2$.

The experiment to determine stability of the calcium-free subtilisin mutants was carried out in 10 mM Tris-HCl, pH 8.0, 50 mM NaCl and 10 mM EDTA (the association constant of EDTA for calcium is $2 \times 10^8$ M$^{-1}$). The proteins were dissolved in this buffer and heated to 55° C. Aliquots were removed at intervals and the activity remaining in each aliquot was determined. The kinetics of inactivation are plotted in FIG. 10. Under these conditions, the half-life of the subtilisin mutants was much improved over that of subtilisin BPN'. These results indicate that subtilisins which have been mutated to eliminate calcium binding at site A have full catalytic activity and improved stability in EDTA relative to subtilisin BPN'. A reasonable level of stability in S46 was achieved even without additional mutations to compensate for lost interactions resulting from deleting amino acids 75–83.

The inactivation of subtilisin in excess calcium is diagramed in the following mechanism:

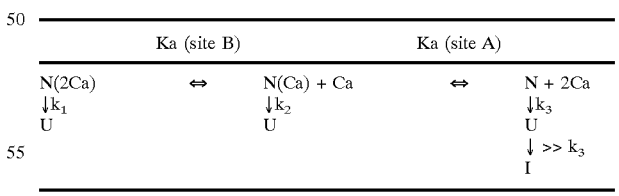

In excess calcium (e.g. ≧1 mM) and moderate temperature, calcium binding and dissociation is in rapid equilibrium because calcium binding is much faster than unfolding. The rate of inactivation is determined by the fraction of each native species times its unfolding rate. Using the above mechanism, one can show that calcium dependent stabilization of subtilisin is dominated by site A rather than site B. The rate of inactivation of BPN' at 65° C. as a function of calcium concentration fits the data to the following mechanism:

$$N(Ca_2) \underset{\downarrow 0.0035 \text{ s}^{-1}}{\overset{33 M^{-1}}{\Leftrightarrow}} N(Ca) + Ca \underset{\downarrow 0.0085 \text{ s}^{-1}}{\overset{2.5 \times 10^5 M^{-1}}{\Leftrightarrow}} N + 2Ca$$
$$U \qquad\qquad U \qquad\qquad \downarrow 8.7 \text{ s}^{-1}$$
$$\qquad\qquad\qquad\qquad\qquad\qquad U$$
$$\qquad\qquad\qquad\qquad\qquad\qquad \downarrow > 25 \text{ s}^{-1}$$
$$\qquad\qquad\qquad\qquad\qquad\qquad I$$

The mechanism predicts that $K_a$'s of site A and site B are $2.5 \times 10^5$ M$^{-1}$ and 33 M$^{-1}$ at 65°. The rate of inactivation of subtilisin with only site A occupied (NCa) is about 1000-times slower than apo-subtilisin (N) and the rate of inactivation with both sites occupied (NCa$_2$) is about 2.5-times slower than with only site A occupied.

The second prediction has been borne out by measuring the calcium dependent stability of a mutant which has site B but lacks site A (Strausberg et al, *Bio/Tech.* 13:669–673 (1995)). The calcium-binding loop is formed from a nine amino acid bubble in the last turn of a 14-residue α-helix involving amino acids 63–85 (McPhalen & James, *Biochem.* 27:6582–6598 (1988)). Deleting amino acids 75–83 creates an uninterrupted helix and abolishes the calcium binding potential at site A (Almog et al, *Proteins* 31:21–32 (1998); Bryan et al, *Biochem.* 31:49374945 (1992)). The x-ray structure has shown that except for the region of the deleted calcium-binding loop, the structure of the mutant and wild type protein are remarkably similar considering the size of the deletion. The structures of subtilisin with and without the deletion superimpose with an rms difference between 261 Cα positions of 0.17 Å. The N-terminus of the wild-type protein lies beside the site A loop, furnishing one calcium coordination ligand, the side chain oxygen of Q2. In Δ75–83 subtilisin, the loop is gone, but the helix is uninterrupted and shows normal helical geometry over its entire length. The rate of inactivation of Δ75–83 subtilisin is only 2.4-times slower in 10 mM CaCl$_2$, 50 mM NaCl than in 10 mM EDTA, 50 mM NaCl.

Another prediction of this last mechanism is that any mutations which stabilize only in the presence of calcium will increase the binding constant for calcium to one or both of the calcium sites. This can be either through effects on the binding sites themselves, as proposed for mutations A116E, G131D, P172D, S63D, N76D and S78D (Pantoliano et al, *Biochem.* 28:7205–7213 (1989); Pantoliano et al, *Biochem.* 27:8311–8317 (1988); Rollence et al, *CRC Crit. Rev. Biotech.* 8:217–224 (1988)), or through indirect effects on conformational stability as seen for mutations S9A, I31L, S53T, L126I, E 156S, G166S, G169A, S188P and T254A. The indirect effect on calcium binding arises because apo-subtilisin displays a loss of cooperativity in the unfolding reaction (Bryan et al, *Biochem.* 31:49374945 (1992)). Thus many mutations which stabilize in the presence of calcium do not stabilize in the presence of EDTA, because they do not influence the rate determining step in the unfolding of apo-subtilisin. In fact, most mutations in natural subtilisins identified to date stabilize only in the presence of calcium. These mutants increase calcium binding affinity because they preferentially stabilize NCa relative to N. The premise that the effects of this class of mutations indirectly increase calcium affinity by increasing general stability was tested using S88, a stabilize version of 75–83 subtilisin (Strausberg et al. 1995). The mutations S9A, I31L, E156S, G166S, G169A, N212G, S188P, K217L and T254A were introduced into the S88 version of Δ75–83 subtilisin (see Table VI).

TABLE VI

| Mutation | Increase in stabilization over S88 subtilisin in either calcium or EDTA |
|---|---|
| S9A | 1.8 |
| I31L | 1.5 |
| L126I | 2.0 |
| E156S | 1.2 |
| G166S | 2.3 |
| G169A | 5.0 |
| N212G | 1.5 |
| M222Q | 2.0 |
| S188P | 1.3 |
| T254A | 3.3 |
| Combined in S88 subtilisin | 1000 |

Because the unfolding of the S88 subtilisin is cooperative in EDTA, these mutations now stabilize subtilisin S88, independent of calcium concentration, to approximately the same extent that they stabilize subtilisin BPN' in 50 mM Tris-HCl, pH 8.0, 50 mM NaCl, 10 mM CaCl$_2$.

Thus, the present inventors have provided convincing evidence that subtilisin mutants may be obtained which remain active and yet do not bind calcium. It is expected therefore that these mutants may be utilized in industrial environments that comprise chelating agents. While this has only been specifically shown with subtilisin BPN', equivalent mutations should work with other serine proteases as well, most particularly other I-S1 or I-S2 subtilisins given that these subtilisins possess substantial sequence similarity, especially in the calcium binding site.

Such strategies, for example, may involve comparing the sequence of subtilisin BPN' to other serine proteases in order to identify the amino acids which are suspected to be necessary for calcium binding and then making suitable modifications, e.g., by site-specific mutagenesis. Since many subtilisins are related to subtilisin BPN' not only through their primary sequences and enzymological properties, but also by X-ray crystallographic data, it is expected that other active subtilisin mutants which lack calcium binding may be produced by site specific mutagenesis. For example, structural evidence exists that the homologous enzyme subtilisin Carlsberg also comprises two calcium binding sites. Similarly, the X-ray structure of thermitase is known and this subtilisin has an analogous calcium A binding-site to that of subtilisin BPN'. For thermitase, the calcium binding loop is a ten residue interruption at the identical site in helix C. Accordingly, these enzymes should also be amenable to the mutations described herein which eliminate the calcium binding site and produce a stable, active enzyme. Moreover, as discussed supra, Siezen et al, has demonstrated that the primary calcium binding site in all subtilisins in groups I-S1 and I-S2 are formed from almost identical nine residue loops in the identical position of helix C. Thus, in view of the almost identical structures of the calcium A-sites, the methods described herein should be applicable to most if not all of the subtilisins in groups I-S1 and I-S2 set forth in Siezen et al.

Alternatively, if the amino acids which comprise the calcium binding sites are already known for a particular subtilisin, the corresponding DNA will be mutated by site specific mutagenesis to delete one or more of such amino acids, or to provide substitution, deletion or addition mutations which eliminate calcium binding.

The subject mutant subtilisins will generally be produced by recombinant methods, in particular by expression of a subtilisin DNA which has been mutated such that upon expression it results in a subtilisin protein which is enzymatically active and which does not bind calcium.

Preferably, the subtilisin DNA's will be expressed in microbial host cells, in particular *Bacillus subtilis*, because this bacteria naturally produces subtilisin, is an efficient secretor of proteins, and is able to produce the protein in an active conformation. However, the invention is not restricted to the expression of the subtilisin mutant in Bacillus, but rather embraces expression in any host cell which provides for expression of the desired subtilisin mutants. Suitable host cells for expression are well known in the art and include, e.g., bacterial host cells such as *Escherichia coli*, Bacillus, Salmonella, Pseudomonas; yeast cells such as *Saccharomyces cerevisiae, Pichia pastoris*, Kluveromyces, Candida, Schizosaccharomyces; and mammalian host cells such as CHO cells. Bacterial host cells, however, are the preferred host cells for expression.

Expression of the subtilisin DNA will be provided using available vectors and regulatory sequences. The actual selection will depend in large part upon the particular host cells which are utilized for expression. For example, if the subtilisin mutant DNA is expressed in Bacillus, a Bacillus promoter will generally be utilized as well as a Bacillus derived vector. The present inventors in particular used the pUB110-based expression vector and the native promoter from the subtilisin BPN' gene to control expression on Bacillus subtilis.

It is further noted that once the amino acid sequence of a particular subtilisin mutant which does not bind calcium has been elucidated, it may also be possible to make the subtilisin mutant by protein synthesis, e.g., by Merrifield synthesis. However, expression of the subtilisin mutants in microbial host cells will generally be preferred since this will allow for the microbial host cell to produce the subtilisin protein in a proper conformation for enzymatic activity. However, since the present inventors further teach herein a method for obtaining in vitro refolding of the subtilisin mutant, it should be possible to convert improperly folded subtilisin mutants into an active conformation.

In order to further illustrate the present invention and the advantages thereof, the following specific examples are given, it being understood that the same is intended only as illustrative and in nowise limitative.

EXAMPLES

Example 1

Cloning and Expression The subtilisin gene from *Bacillus amyloliquefaciens* (subtilisin BPN') has been cloned, sequenced, and expressed at high levels from its natural promoter sequences in *Bacillus subtilis* (Wells et al., *Nucleic Acids Res.* 11:7911–7925 (1983); Vasantha et al., *J. Bacteriol.* 159:811819(1984)). All mutant genes were recloned into a pUB110-based expression plasmid and used to transform *B. subtilis*. The *B. subtilis* strain used as the host contains a chromosomal deletion of its subtilisin gene and therefore produces no background wild type (wt) activity (Fahnestock et al., *Appl. Environ. Microbial.* 53:379–384 (1987)). Oligonucleotide mutagenesis was carried out as previously described. (Zoller et al., *Methods Enzymol.* 100:468–500 (1983); Bryan et al., *Proc. Natl. Acad. Sci.* 83:3743–3745 (1986b)). S221C was expressed in a 1.51 New Brunswick fermentor at a level of approximately 100 mg of the correctly processed mature form per liter. The addition of wild type subtilisin to promote production of the mature form of S221C subtilisin was not required in our bacillus host strain as was the case for prior strains (Abrahmsen et al., *Biochemistry* 30:4151–4159 (1991)).

Protein Purification & Characterization. Wild type subtilisin and the variant enzymes were purified and verified for homogeneity essentially as described in Bryan et al., *Proc. Natl. Acad. Sci.* 83:3743–3745 (1986b); Pantoliano et al., *Biochemistry* 26:2077–2082 (1987); and *Biochemistry* 27:8311–8317 (1988). In some cases the C221 mutant subtilisins were re-purified on a sulfhydryl specific mercury affinity column (Affi-gel 501, Biorad). Assays of peptidase activity were performed by monitoring the hydrolysis of succinyl-(L)Ala-(L)-Ala-(L)-Pro-(L)-Phe-p-nitroanilide, hereinafter sAAPFna, as described by DelMar et al., *Anal Biochem.* 99:316–320 (1979). The protein concentration, [P], was determined using $P^{0.1\%}=1.17$ at 280 mn (Pantoliano et al, *Biochemistry* 28:7205–7213 (1989)). For variants which contain the Y217K change, the $p^{0.1\%}$ at 280 nm was calculated to be 1.15 (or 0.96×X wt), based on the loss of one Tyr residue (Pantoliano et al., *Biochemistry* 28:7205–7213 (1989)).

N-terminal Analysis The first five amino acids of subtilisin S 15 were determined by sequential Edman degradation and HPLC analysis. This revealed that 100% of the material had the amino acid sequence expected from the DNA sequence of the gene and that processing of the pro-peptide was at the same position in the sequence for the mutant as for the wild type enzyme.

Example 2

Structure of the calcium A site of S12 subtilisin Calcium at site A is coordinated by five carbonyl oxygen ligands and one aspartic acid. Four of the carbonyl oxygen ligands to the calcium are provided by a loop composed of amino acids 75–83 (FIG. 2). The geometry of the ligands is that of a pentagonal bipyramid whose axis runs through the carbonyls of 75 and 79. On one side of the loop is the bidentate carboxylate (D41), while on the other side is the N-terminus of the protein and the side chain of Q2. The seven coordination distances range from 2.3 to 2.6 A, the shortest being to the aspartyl carboxylate. Three hydrogen bonds link the N-terminal segment to loop residues 78–82 in parallel-beta arrangement.

Preparation of apo-subtilisin S11 and S12 subtilisin contain an equal molar amount of tightly bound calcium after purification. X-ray crystallography has shown this calcium to be bound to the A site (Finzel et al., *J. Cell. Biochem. Suppl.* 10A:272 (1986); Pantoliano et al., *Biochemistry* 27:8311–8317 (1988); McPhalen et al., *Biochemistry* 27:6582–6598 (1988)).

Complete removal of calcium from subtilisin is very slow, requiring 24 hours of dialysis against EDTA at 25° C. to remove all calcium from the protein and then 48 more hours of dialysis in high salt (Brown et al., *Biochemistry* 16:3883–3896 (1977)) at 4° C. to remove all EDTA from the protein. To prepare the calcium-free form of subtilisins S 11 and S12, 20 mg of lyophilized protein was dissolved in 5 ml of 10 mM EDTA, 10 mM tris(hydroxymethyl)aminomethane hydrochloric acid (hereinafter Tris-HCl) at pH 7.5 and dialyzed against the same buffer for 24 hours at 25° C. In order to remove EDTA, which binds to subtilisin at low ionic strength, the protein was then dialyzed twice against 2 liters of 0.9M NaCl, 10 mM Tris-HCl at pH 7.5 at 4° C. for a total of 24 hours and then three times against 2 liters of 2.5 mM Tris-HCl at pH 7.5 at 4° C. for a total of 24 hours. Chelex 100 was added to all buffers not containing EDTA. When versions of C221 subtilisin not containing stabilizing amino acid substitutions were used, up to 50% of the protein-precipitated during this procedure. It is essential to use pure native apoenzyme in titration experiments so that spurious heat produced by precipitation upon the addition of calcium does not interfere with the measurement of the heat of binding.

To ensure that preparations of apo-subtilisin were not contaminated with calcium or EDTA, samples were checked by titration with calcium in the presence of Quin2 prior to performing titration calorimetry.

Titration Calorimetry Measurements The calorimetric titrations were performed with a Microcal Omega titration calorimeter as described in detail by Wiseman et al., *Analytical Biochemistry* 179:131–137 (1989). The titration calorimeter consists of a matched reference cell containing the buffer and a solution cell (1.374 mL) containing the protein solution. Microliter aliquots of the ligand solution are added to the solution cell through a rotating stirrer syringe operated with a plunger driven by a stepping motor. After a stable baseline was achieved at a given temperature, the automated injections were initiated and the accompanying heat change per injection was determined by a thermocouple sensor between the cells. During each injection, a sharp exothermic peak appeared which returned to the baseline prior to the next injection occurring 4 minutes later. The area of each peak represents the amount of heat accompanying binding of the added ligand to the protein. The total heat (Q) was then fit by a nonlinear least squares minimization method (Wiseman et al., *Analytical Biochemistry* 179:131–137 (1989)) to the total ligand concentration, $[Ca]_{total}$, according to the equation:

$$dQ/d[Ca]_{total} = \Delta H[1/2 + (1-(1+r)/2 - X_r/2)/X_r - 2X_r(1-r) + 1 + r^2)^{1/2}] \quad (1)$$

wherein $1/r = [P]_{total} \times K_a$ and $X_r = [Ca]_{total}/[P]_{total}$.

The binding of calcium to the S11 and S12 subtilisins was measured by titration calorimetry as it allows both the binding constant and the enthalpy of binding to be determined (Wiseman et al., *Analytical Biochemistry* 179:131–137 (1989); Schwarz et al., *J. Biol. Chem.* 266:24344–24350 (1991)).

The S 11 and S12 subtilisin mutants were used in titration experiments because production of the wild type apoenzyme is impossible due to its proteolytic activity and low stability. Titrations of S11 and S12 were performed at protein concentrations [P]=30 μM and 100 μM. Titration of the S11 apoenzyme with calcium at 25° C. is shown in FIG. 4. The data points correspond to the negative heat of calcium binding associated with each titration of calcium. The titration calorimeter is sensitive to changes in Ka under conditions at which the product of $K_a \times [P]$ is between 1 and 1000 (Wiseman et al., *Analytical Biochemistry* 179:131–137 (1989)). Since the $K_a$ for subtilisin is about $1 \times 10^7$ M$^{-1}$, these protein concentrations result in values of $K_a \times [P] = 300$ and 1000. At lower protein concentrations the amount of heat produced per titration is difficult to measure accurately.

The results of fitting the titrations of S11 and S12 to a calculated curve are summarized in Table 2. The parameters in the table include binding parameters for stoichiometric ratio (n), binding constant ($K_a$) and binding enthalpy ($\Delta H$). These parameters were determined from deconvolution using nonlinear least squares minimization (Wiseman et al., *Analytical Biochemistry* 179:131–137 (1989)). Measurements for each experimental condition were performed in duplicate at 25° C. The protein concentrations ranged from 30 to 100 μM while the concentration of the calcium solutions were about 20 times the protein concentrations. Each binding constant and enthalpy were based on several titration runs at different concentrations. Titration runs were performed until the titration peaks were close to the baseline.

TABLE 2

Titration Calorimetry of the Calcium A Site in Subtilisin Mutants S11 and S12.

| | | Parameters calculated from fit | | |
|---|---|---|---|---|
| Mutant | [P] | n | $K_a$ | $\Delta H$ |
| S11 | 100 μM | 0.98 ± 0.01 | 7.8 ± 0.2 × 10$^6$ | −11.3 ± 0.1 |
| S11 | 33 μM | 0.9 ± 0.3 | 6.8 ± 1.5 × 10$^6$ | −10.9 ± 0.2 |
| S12 | 100 μM | 0.99 ± 0.01 | 6.4 ± 0.2 × 10$^6$ | −11.8 ± 0.5 |

The average values obtained are similar for S11 and S12: $\Delta H = \sim -11$ kcal/mol; $K_a = 7 \times 10^6$ M$^{-1}$ and a stoichiometry of binding of 1 calcium site per molecule. The weak binding site B does not bind calcium at concentrations below the millimolar range, and therefore does not interfere with measurement of binding to the binding site A. The standard free energy of binding at 25° C. is 9.3 kcal/mol. The binding of calcium is therefore primarily enthalpically driven with only a small net loss in entropy ($\Delta S_{binding} = -6.7$ cal/° mol).

Example 3

In vitro refolding of S15 subtilisin. For refolding studies subtilisin was maintained as a stock solution in 2.5 mM Tris-HCl at pH 7.5 and 50 mM KCl at a concentration of approximately 100 μM. The protein was denatured by diluting the stock solution into 5M guanidine hydrochloride (Gu-HCl) at pH 7.5 or in most cases into 25 mM H$_3$PO$_4$ or HCl at pH 1.8–2.0. The fmal concentration of protein was 0.1 to 5 μM. S15 was completely denatured in less than 30 seconds by these conditions. S12 required approximately 60 minutes to become fully denatured. Acid-denatured protein was then neutralized to pH 7.5 by the addition of Tris-base (if denatured in HCl) or 5M NaOH (if denatured in H$_3$PO$_4$). Refolding was initiated by the addition of KCl, NaCl or CaCl$_2$ to the desired concentration. For example, KCl was added from a stock solution of 4M to a final concentration of 0.1 to 1.5M with rapid stirring. In most cases renaturation was carried out at 25° C. The rate of remturation was determined spectrophotometrically by uv absorption from the increase in extinction at λ=286, from the increase in intrinsic tyrosine and tryptophan fluorescence (excitation λ=282, emission λ–347), or by circular dichroism from the increase in negative ellipticity at λ=222 nm.

Example 4

X-ray Crystallography. Large single crystal growth and X-ray diffraction data collection were performed essentially as previously reported (Bryan et al., *Proteins: Struct. Funct. Genet.* 1:326–334 (1986a); Pantoliano et al., *Biochemistry* 27:8311–8317 (1988); Pantoliano et al., *Biochemistry* 28:7205–7213 (1989)) except that it was not necessary to inactivate the S221C variants with diisopropyl fluorophosphate (DFP) in order to obtain suitable crystals. The starting model for S12 was made from the hyperstable subtilisin mutant 8350 (Protein Data Bank entry ISO1.pdb). The S12 structure was refmed and then modified to provide the starting model for S15.

Data sets with about 20,000 reflections between 8.0 Å and 1.8 Å resolution were used to refine both models using restrained least-squares techniques (Hendrickson et al., "Computing in Crystallography" in Diamond et al., eds., *Bangalore: Indian Institute of Science* 13.01–13.23 (1980)). Initial difference maps for S15, phased by a version of S12 with the entire site A region omitted, clearly showed continuous density representing the uninterrupted helix, permitting an initial S15 model to be constructed and refinement begun. Each mutant was refmed from R approximately 0.30 to R approximately 0.18 in about eighty cycles, interspersed with calculations of electron density maps and manual adjustments using the graphics modeling program FRODO (Jones, *J. Appl. Crystallogr.* 11:268–272 (1978)).

Except for the region of the deleted calcium-binding loop, the structures of S12 and S15 are very similar, with a root mean square (r.m.s) deviation of 0.18 Å between 262 α-carbons. The N-terminus of S12 (as in the wild-type) lies beside the site A loop, furnishing one calcium coordination ligand, the side chain oxygen of Q2. In S15 the loop is gone, leaving residues 1–4 disordered. In S12 (as in wild type) the site A loop occurs as an interruption in the last turn of a 14-residue alpha helix; in S15 this helix is uninterrupted and shows normal helical geometry over its entire length. Diffuse difference density and higher temperature factors indicate some disorder in the newly exposed residues adjacent to the deletion.

Example 5

Differential Scanning Calorimetry The stability properties of S12 and S15 were studied using DSC (differential scanning calorimetry). The Δ75–83 mutant (S15) is very similar in melting temperature to the apoenzyme of S12. The DSC profiles of apo-S12 and S15 are shown in FIG. 3. The temperature of maximum heat capacity is 63.0° C. for S15 and 63.5° C. for apo-S12 at pH 9.63. The DSC experiments were carried out at high pH to avoid aggregation during the denaturation process. The amount of excess heat absorbed by a protein sample as the temperature increased through a transition from the folded to unfolded state at constant pressure, which provided a direct measurement of the ΔH of unfolding (Privalov et al., *Methods Enzymol.* 131:4–51 (1986)). $\Delta H_{cal}$ of unfolding for apo-S12 and S15 is about 140 kcal/mol. Above pH 10.0, the unfolding transition for S15 fit a two-state model reasonably well, consistent with equilibrium thermodynamics as expressed in the van't Hoff equation (dln K/dT=$\Delta H_{vH}$/(RT$^2$)) with $\Delta H_{vH}$ (the van't Hoff enthalpy or apparent enthalpy) approximately equal to $\Delta H_{cal}$ (the calorimetric or true enthalpy). At pH 9.63, however, the melting profile for both proteins was asymmetric indicating that the unfolding is not a pure two-state process.

Example 6

Figure 5A:
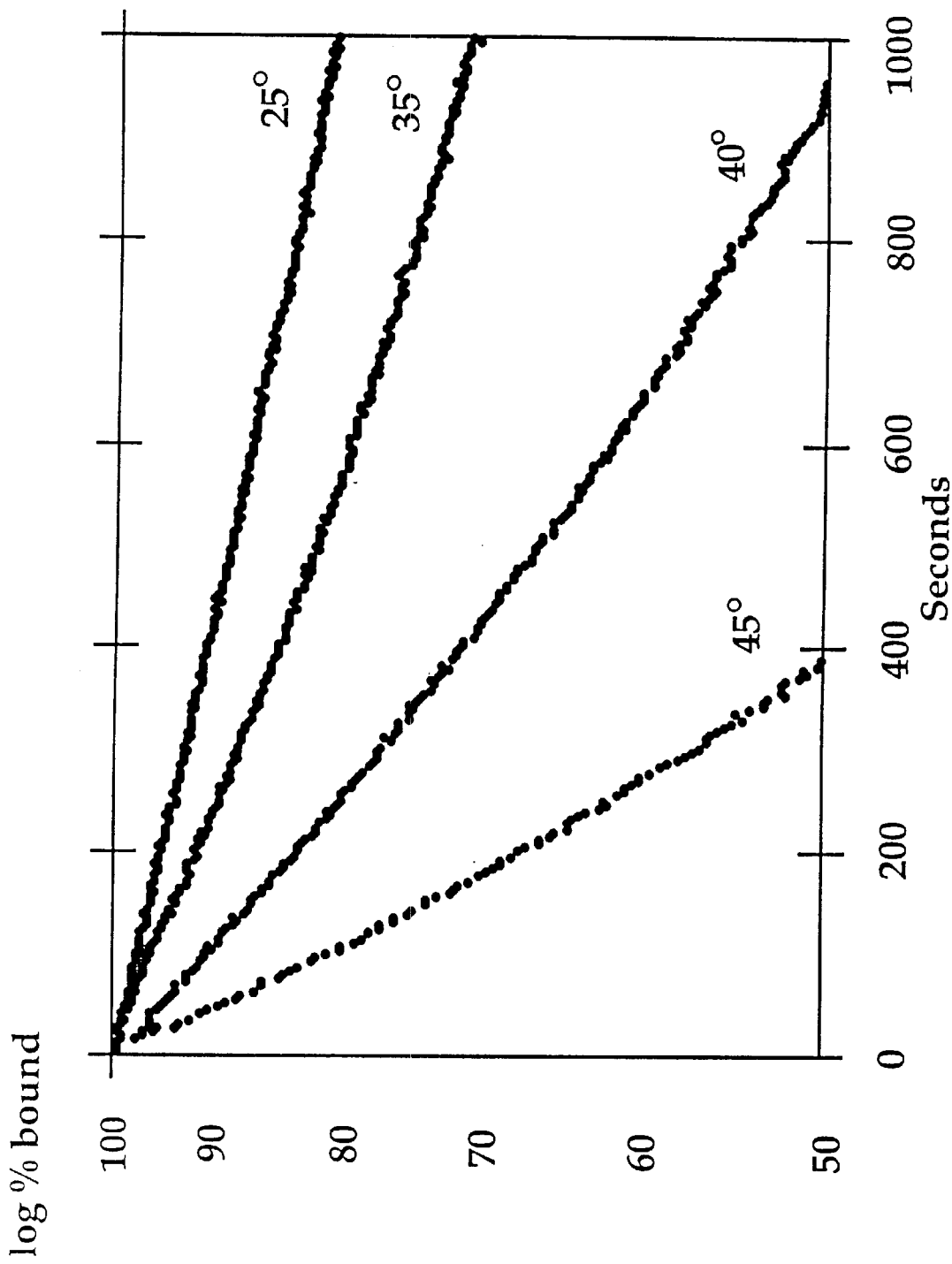

Measuring kinetics of calcium dissociation. The dissociation of calcium from subtilisin is a slow process. To measure this rate the fluorescent calcium chelator Quin 2 was used. Quin 2 binds calcium with a $K_a$ of $1.8 \times 10^8$ at pH 7.5 (Linse et al., *Biochemistry* 26:6723–6735 (1987)). The fluorescence of Quin 2 at 495 nm increases by approximately 6-fold when bound to calcium (Bryant, *Biochem. J.* 226:613–616 (1985)). Subtilisin S11 or S12 as isolated contains one calcium ion per molecule. When mixed with an excess of Quin 2, the kinetics of calcium release from the protein can be followed from the increase in fluorescence at 495 nm. The reaction is assumed to follow the pathway N(Ca)↔N+Ca+Quin 2↔Quin(Ca). The dissociation of calcium front subtilisin is very slow relative to calcium binding by Quin 2, such that the change in fluorescence of Quin 2 is equal to the rate of calcium dissociation from subtilisin. As can be seen in FIG. 5*a*, the initial release of calcium from S11 follows simple first order kinetics.

Figure 5B:
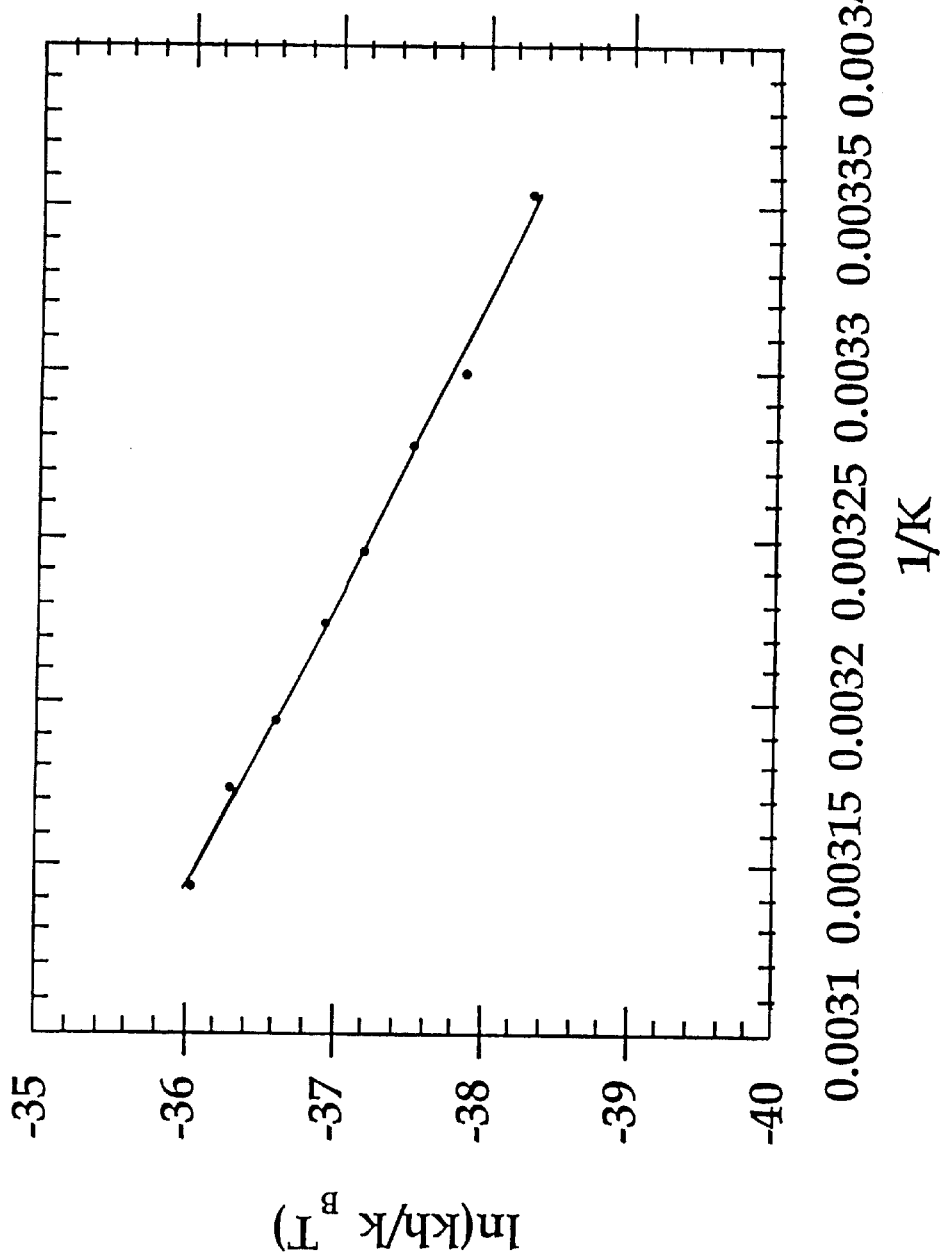

Temperature dependence of calcium dissociation The first order rate constant (k) for calcium dissociation was measured from 200 to 45° C. The plot of ln k vs. 1/T°K is roughly linear. The calcium dissociation data was curve fit using transition state theory according to the Erying equation:

$$\Delta G^{\ddagger} = -RT \ln K^{\ddagger} = -RT \ln kh/k_B T \qquad (2)$$

wherein $k_B$ is the Boltzman constant, h is Planck's constant and k is the first order rate constant for folding. A graph of ln hk/$k_B$T vs. 1/T is shown in FIG. 5*b*.

The data was then curve fit according to the equation (Chen et al., *Biochemistry* 28:691–699 (1989)):

$$\ln K^{\ddagger} = A + B(To/T) + C \ln (To/T) \qquad (3)$$

wherein A=[$\Delta Cp^{\ddagger}+\Delta S^{\ddagger}$(To)]/R; B=A–$\Delta G^{\ddagger}(T_o)$/RTo; C=$\Delta Cp^{\ddagger}$/R. The data obtained yields the following results: $\Delta G^{\ddagger}$=22.7 kcal/mol; $\Delta Cp'^{\ddagger}$=–0.2 kcal/°mol; $\Delta S'^{\ddagger}$=–10 cal/°mol; and $\Delta H'^{\ddagger}$=19.7 kcal/mol at a reference temperature of 25° C. A possible slight curvature of the plot would be due to a change in heat capacity associated with formation of the transition state ($\Delta Cp'^{\ddagger}$=0.2 kcal/°mol). ΔCp for protein folding has been shown to be closely correlated with a change in exposure of hydrophobic groups to water (Privalov et al., *Adv. Protein Chem.* 39:191–234 (1988); Livingstone et al., *Biochemistry* 30:4237–4244 (1991)). In terms of heat capacity, the transition state therefore appears similar to the native protein. The values for $\Delta S'^{\ddagger}$ and $\Delta H'^{\ddagger}$ obtained from FIG. 5*b* indicate that the transition state is enthalpically less favorable than the calcium bound form with only a small change in entropy.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

All references cited herein are incorporated in their entirety, as if individually incorporated by reference.

What is claimed is:

1. A subtilisin protein which has been mutated to eliminate the ability of said subtilisin protein to bind calcium at the calcium A binding site wherein the mutated subtilisin protein comprises a deletion of amino acids 75–83 and a deletion of part or all of the N-terminal region amino acids 1–22, wherein said amino acid positions are numbered according to correspondence with the amino acid positions of the amino acid sequence of subtilisin BPN' set forth in SEQ ID NO. 1.

2. The subtilisin protein of claim 1, wherein amino acids 1–22 of the N-terminal region are deleted.

3. The subtilisin protein of claim 1, wherein amino acids 1–17 of the N-terminal region are deleted.

4. The subtilisin protein of claim 1, wherein the subtilisin is from a Bacillus strain.

5. The subtilisin protein of claim 4, wherein the subtilisin mutant is a subtilisin BPN' mutant, a subtilisin Carlsberg mutant, a subtilisin DY mutant, a subtilisin amylosacchariticus mutant or a subtilisin mesenticopeptidase mutant or a subtilisin Savinase mutant.

6. The subtilisin protein of claim 5, wherein the subtilisin mutant is a subtilisin BPN' mutant.

7. The subtilisin protein of claim 1, wherein said protein also contains one or more substitutions selected from the group consisting of S221C, Y217K, P5A, M50F, N218S, P5S, Q2K, A73L, Q206V, Q206C, S3C, K43N, Q217E, S9A, I31L, E156S, G166S, G169A, S188P, N212G, K217L, T254A, L126I, and M222Q.

8. The subtilisin protein of claim 1, wherein one or more substitutions are also made at amino acid positions: 41–45; 70–74; 86–87; 181–184; 200–214; 226–237; and 267–275.

9. A recombinant method which provides for the expression of a subtilisin protein which has been mutated to eliminate the ability of said subtilisin protein to bind calcium at the calcium A binding site, wherein the mutated subtilisin protein comprises a deletion of amino acids 75–83 and a deletion of part or all of the N-terminal region amino acids 1–22, wherein said amino acid positions are numbered according to correspondence with the amino acid positions of the amino acid sequence of subtilisin BPN' set forth in SEQ ID NO. 1, said method comprising:

(a) transforming a recombinant host cell with an expression vector comprising a DNA sequence encoding an enzymatically active subtilisin which does not bind calcium and which has a deletion of part or all of the N-terminal region amino acids 1–22;

(b) culturing said host cells under conditions which provide for the expression of the enzymatically active subtilisin mutant; and (c) recovering the expressed enzymatically active subtilisin mutant from said microbial host.

10. The recombinant method of claim 9, wherein the subtilisin mutant is a subtilisin BPN' mutant.

11. The recombinant method of claim 10, wherein the subtilisin BPN' DNA comprises one or more additional mutations which provide for enhanced thermal stability or which provide for restoration of cooperativity of folding of the subtilisin protein.

12. The recombinant method of claim 9, wherein the mutated subtilisin protein also has one or more substitutions selected from the group consisting of S221C, Y217K, P5A, M50F, N218S, P5S, Q2K, A73L, Q206V, Q206C, S3C, K43N, Q217E, S9A, I31L, E156S, G166S, G169A, S188P, N212G, K217L, T254A, L126I, and M222Q.

13. The recombinant method of claim 9, wherein mutated subtilisin protein also has a substitution at one of the following amino acid positions: 41–45; 70–74; 86–87; 181–184; 200–214; 226–237, and 267–275.

14. A recombinant DNA which encodes the mutated subtilisin protein of claim 1.

* * * * *

SEQUENCE LISTING

<160> NUMBER OF SEQ ID NOS: 2

<210> SEQ ID NO 1
<211> LENGTH: 1868
<212> TYPE: DNA
<213> ORGANISM: Bacillus amyloliquefaciens
<220> FEATURE:

```
<221> NAME/KEY: CDS
<222> LOCATION: (450)..(1595)
<223> OTHER INFORMATION:
<220> FEATURE:
<221> NAME/KEY: mat_peptide
<222> LOCATION: (771)..()
<223> OTHER INFORMATION:

<400> SEQUENCE: 1
tttttccgca attatatcat tgacaatatc aacatcaatg atattcatta tcattatttt     60
tataaaatgg tttcacagct tttctcggtc aagaaagcca aagactgatt tcgcttacgt    120
ttccatcagt cttctgtatt aacaaaaga tgacatttat cctgttttg gaacaacccc     180 caaaaatgga aacaaaccgt tcgacccagg aaacaagcga gtgattgctc ctgtgtacat    240
ttactcatgt ccatccatcg gttttttcca ttaaaattta aatatttcga gttcctacga    300
aacgaaagag agatgatata cctaaataga aataaaacaa tctgaaaaaa attgggtcta    360
ctaaaatatt attccatact atacaattaa tacacagaat aatctgtcta ttggttattc    420
tgcaaatgaa aaaaggaga ggataaaaga gtg aga ggc  aaa aaa gta tgg atc     473
                                  Val Arg Gly  Lys Lys Val Trp Ile
                                     -105                    -100 agt ttg ctg ttt gct tta gcg tta atc ttt acg atg gcg ttc ggc agc      521
Ser Leu Leu Phe Ala Leu Ala Leu Ile Phe Thr Met Ala Phe Gly Ser
            -95                 -90                 -85 aca tcc tct gcc cag gcg gca ggg aaa tca aac ggg gaa aag aaa tat      569
Thr Ser Ser Ala Gln Ala Ala Gly Lys Ser Asn Gly Glu Lys Lys Tyr
        -80                 -75                 -70 att gtc ggg ttt aaa cag aca atg agc acg atg agc gcc gct aag aag      617
Ile Val Gly Phe Lys Gln Thr Met Ser Thr Met Ser Ala Ala Lys Lys
    -65                 -60                 -55 aaa gat gtc att tct gaa aaa ggc ggg aaa gtg caa aag caa ttc aaa      665
Lys Asp Val Ile Ser Glu Lys Gly Gly Lys Val Gln Lys Gln Phe Lys
   -50                 -45                 -40 tat gta gac gca gct tca gct aca tta aac gaa aaa gct gta aaa gaa      713
Tyr Val Asp Ala Ala Ser Ala Thr Leu Asn Glu Lys Ala Val Lys Glu
-35                 -30                 -25                 -20 ttg aaa aaa gac ccg agc gtc gct tac gtt gaa gaa gat cac gta gca      761
Leu Lys Lys Asp Pro Ser Val Ala Tyr Val Glu Glu Asp His Val Ala
                -15                 -10                  -5 cat gcg tac gcg cag tcc gtg cct tac ggc gta tca caa att aaa gcc      809
His Ala Tyr Ala Gln Ser Val Pro Tyr Gly Val Ser Gln Ile Lys Ala
        -1  1                 5                  10 cct gct ctg cac tct caa ggc tac act gga tca aat gtt aaa gta gcg      857
Pro Ala Leu His Ser Gln Gly Tyr Thr Gly Ser Asn Val Lys Val Ala
    15                  20                  25 gtt atc gac agc ggt atc gat tct tct cat cct gat tta aag gta gca      905
Val Ile Asp Ser Gly Ile Asp Ser Ser His Pro Asp Leu Lys Val Ala
30                  35                  40                  45 ggc gga gcc agc atg gtt cct tct gaa aca aat cct ttc caa gac aac      953
Gly Gly Ala Ser Met Val Pro Ser Glu Thr Asn Pro Phe Gln Asp Asn
                50                  55                  60 aac tct cac gga act cac gtt gcc ggc aca gtt gcg gct ctt aat aac     1001
Asn Ser His Gly Thr His Val Ala Gly Thr Val Ala Ala Leu Asn Asn
            65                  70                  75 tca atc ggt gta tta ggc gtt gcg cca agc gca tca ctt tac gct gta     1049
Ser Ile Gly Val Leu Gly Val Ala Pro Ser Ala Ser Leu Tyr Ala Val
        80                  85                  90 aaa gtt ctc ggt gct gac ggt tcc ggc caa tac agc tgg atc att aac     1097
Lys Val Leu Gly Ala Asp Gly Ser Gly Gln Tyr Ser Trp Ile Ile Asn
    95                  100                 105
```

-continued

```
gga atc gag tgg gcg atc gca aac aat atg gac gtt att aac atg agc    1145
Gly Ile Glu Trp Ala Ile Ala Asn Asn Met Asp Val Ile Asn Met Ser
110             115                 120                 125 ctc ggc gga cct tct ggt tct gct gct tta aaa gcg gca gtt gat aaa    1193
Leu Gly Gly Pro Ser Gly Ser Ala Ala Leu Lys Ala Ala Val Asp Lys
            130                 135                 140 gcc gtt gca tcc ggc gtc gta gtc gtt gcg gca gcc ggt aac gaa ggc    1241
Ala Val Ala Ser Gly Val Val Val Val Ala Ala Ala Gly Asn Glu Gly
        145                 150                 155 act tcc ggc agc tca agc aca gtg ggc tac cct ggt aaa tac cct tct    1289
Thr Ser Gly Ser Ser Ser Thr Val Gly Tyr Pro Gly Lys Tyr Pro Ser
    160                 165                 170 gtc att gca gta ggc gct gtt gac agc agc aac caa aga gca tct ttc    1337
Val Ile Ala Val Gly Ala Val Asp Ser Ser Asn Gln Arg Ala Ser Phe
175                 180                 185 tca agc gta gga cct gag ctt gat gtc atg gca cct ggc gta tct atc    1385
Ser Ser Val Gly Pro Glu Leu Asp Val Met Ala Pro Gly Val Ser Ile
190                 195                 200                 205 caa agc acg ctt cct gga aac aaa tac ggg gcg tac aac ggt acg tca    1433
Gln Ser Thr Leu Pro Gly Asn Lys Tyr Gly Ala Tyr Asn Gly Thr Ser
            210                 215                 220 atg gca tct ccg cac gtt gcc gga gcg gct gct ttg att ctt tct aag    1481
Met Ala Ser Pro His Val Ala Gly Ala Ala Ala Leu Ile Leu Ser Lys
        225                 230                 235 cac ccg aac tgg aca aac act caa gtc cgc agc agt tta gaa aac acc    1529
His Pro Asn Trp Thr Asn Thr Gln Val Arg Ser Ser Leu Glu Asn Thr
    240                 245                 250 act aca aaa ctt ggt gat tct ttc tac tat gga aaa ggg ctg atc aac    1577
Thr Thr Lys Leu Gly Asp Ser Phe Tyr Tyr Gly Lys Gly Leu Ile Asn
255                 260                 265 gta cag gcg gca gct cag taaaacataa aaaaccggcc ttggccccgc           1625
Val Gln Ala Ala Ala Gln
270                 275 cggttttta ttattttct tcctccgcat gttcaatccg ctccataatc gacggatggc    1685
tccctctgaa aattttaacg agaaacggcg ggttgacccg gctcagtccc gtaacggcca  1745
agtcctgaaa cgtctcaatc gccgcttccc ggtttccggt cagctcaatg ccgtaacggt  1805
cggcggcgtt ttcctgatac cgggagacgg cattcgtaat cggatcagaa gcaaaactga  1865
gca                                                                1868
```

<210> SEQ ID NO 2
<211> LENGTH: 382
<212> TYPE: PRT
<213> ORGANISM: Bacillus amyloliquefaciens

<400> SEQUENCE: 2

```
Val Arg Gly Lys Lys Val Trp Ile Ser Leu Leu Phe Ala Leu Ala Leu
            -105                -100                -95

Ile Phe Thr Met Ala Phe Gly Ser Thr Ser Ser Ala Gln Ala Ala Gly
        -90                 -85                 -80

Lys Ser Asn Gly Glu Lys Lys Tyr Ile Val Gly Phe Lys Gln Thr Met
-75                 -70                 -65                 -60

Ser Thr Met Ser Ala Ala Lys Lys Lys Asp Val Ile Ser Glu Lys Gly
                -55                 -50                 -45

Gly Lys Val Gln Lys Gln Phe Lys Tyr Val Asp Ala Ala Ser Ala Thr
            -40                 -35                 -30

Leu Asn Glu Lys Ala Val Lys Glu Leu Lys Lys Asp Pro Ser Val Ala
```

-continued

```
              -25                  -20                  -15
Tyr Val Glu Glu Asp His Val Ala His Ala Tyr Ala Gln Ser Val Pro
        -10              -5              -1   1              5
Tyr Gly Val Ser Gln Ile Lys Ala Pro Ala Leu His Ser Gln Gly Tyr
                10              15                  20
Thr Gly Ser Asn Val Lys Val Ala Val Ile Asp Ser Gly Ile Asp Ser
                25              30                  35
Ser His Pro Asp Leu Lys Val Ala Gly Gly Ala Ser Met Val Pro Ser
            40              45              50
Glu Thr Asn Pro Phe Gln Asp Asn Asn Ser His Gly Thr His Val Ala
    55                  60                  65
Gly Thr Val Ala Ala Leu Asn Asn Ser Ile Gly Val Leu Gly Val Ala
70                  75              80              85
Pro Ser Ala Ser Leu Tyr Ala Val Lys Val Leu Gly Ala Asp Gly Ser
                90              95              100
Gly Gln Tyr Ser Trp Ile Ile Asn Gly Ile Glu Trp Ala Ile Ala Asn
                105             110             115
Asn Met Asp Val Ile Asn Met Ser Leu Gly Gly Pro Ser Gly Ser Ala
            120             125             130
Ala Leu Lys Ala Ala Val Asp Lys Ala Val Ala Ser Gly Val Val Val
    135             140             145
Val Ala Ala Ala Gly Asn Glu Gly Thr Ser Gly Ser Ser Ser Thr Val
150             155             160             165
Gly Tyr Pro Gly Lys Tyr Pro Ser Val Ile Ala Val Gly Ala Val Asp
            170             175             180
Ser Ser Asn Gln Arg Ala Ser Phe Ser Ser Val Gly Pro Glu Leu Asp
            185             190             195
Val Met Ala Pro Gly Val Ser Ile Gln Ser Thr Leu Pro Gly Asn Lys
        200             205             210
Tyr Gly Ala Tyr Asn Gly Thr Ser Met Ala Ser Pro His Val Ala Gly
    215             220             225
Ala Ala Ala Leu Ile Leu Ser Lys His Pro Asn Trp Thr Asn Thr Gln
230             235             240             245
Val Arg Ser Ser Leu Glu Asn Thr Thr Thr Lys Leu Gly Asp Ser Phe
            250             255             260
Tyr Tyr Gly Lys Gly Leu Ile Asn Val Gln Ala Ala Ala Gln
            265             270             275
```